United States Patent [19]

Kadin

[11] Patent Number: 4,556,672

[45] Date of Patent: Dec. 3, 1985

[54] 3-SUBSTITUTED 2-OXINDOLE-1-CARBOXAMIDES AS ANALGESIC AND ANTI-INFLAMMATORY AGENTS

[75] Inventor: Saul B. Kadin, New London, Conn.

[73] Assignee: Pfizer Inc., New York, N.Y.

[21] Appl. No.: 684,634

[22] Filed: Dec. 21, 1984

Related U.S. Application Data

[63] Continuation-in-part of Ser. No. 590,659, Mar. 19, 1984, abandoned.

[51] Int. Cl.$^4$ .................. A61K 31/40; C07D 209/34
[52] U.S. Cl. ................................. 514/414; 514/253; 514/256; 514/333; 514/339; 514/361; 514/362; 514/363; 514/365; 514/372; 514/374; 514/378; 514/397; 514/406; 514/411; 514/418; 544/333; 544/405; 546/270; 546/273; 548/127; 548/134; 548/136; 548/181
[58] Field of Search ............... 548/450, 431, 468, 486, 548/136, 236, 248, 181, 134, 454, 336, 374, 127, 214, 247; 544/333, 405; 546/273, 270; 514/253, 256, 362, 363, 372, 374, 378, 365, 397, 406, 361, 411, 414, 418, 339

[56] References Cited

U.S. PATENT DOCUMENTS

| | | | |
|---|---|---|---|
| 3,190,889 | 6/1965 | Shen | 548/374 |
| 3,462,450 | 8/1969 | Shen | 260/326.12 |
| 3,519,592 | 7/1970 | Holden | 260/240 |
| 3,631,177 | 12/1971 | Holden | 260/325 |
| 3,634,453 | 1/1972 | McManus et al. | 260/325 |
| 3,749,731 | 7/1973 | Zinnes et al. | 260/306.8 |
| 3,856,967 | 12/1974 | Allais et al. | 424/274 |
| 3,975,531 | 8/1976 | Welstead et al. | 424/274 |
| 4,012,394 | 3/1977 | Deschamps et al. | 546/273 |

FOREIGN PATENT DOCUMENTS

| | | |
|---|---|---|
| 46-14898 | 4/1971 | Japan . |
| 48-14667 | 2/1973 | Japan . |
| 1158532 | 7/1969 | United Kingdom . |
| 1206995 | 9/1970 | United Kingdom . |

OTHER PUBLICATIONS

Pakula et al., *Chemical Abstracts*, 72:12563(k), (1970).
Brenner et al., *Chemical Abstracts*, 72:12565(n), (1970).
Shen et al., *Chemical Abstracts*, 72:12566(p), (1970).
Wenkert et al., *Journal of the American Chemical Society*, 80, 4899, (1958).
Bunnett et al., *Organic Syntheses*, vol. 40, 1, (1960).
El-Enany et al., *Bulletin of the Faculty of Pharmacy*, (Cairo University), 14, 29, (1975).
Buchel et al., *Z. Anal. Chemie*, 190, 243, (1962).

*Primary Examiner*—Donald G. Daus
*Assistant Examiner*—Mary E. Ceperley
*Attorney, Agent, or Firm*—Charles J. Knuth; Peter C. Richardson; J. Trevor Lumb

[57] ABSTRACT

Certain new 2-oxindole-1-carboxamide compounds having an acyl substituent at the 3-position are inhibitors of the cyclooxygenase (CO) and lipoxygenase (LO) enzymes, and are useful as analgesic and anti-inflammatory agents in mammalian subjects. In particular, the compounds of the invention are useful for ameliorating or eliminating pain in human subjects recovering from surgery or trauma, and in alleviating the symptoms of chronic diseases, such as rheumatoid arthritis and osteoarthritis, in human subjects.

65 Claims, No Drawings

3-SUBSTITUTED 2-OXINDOLE-1-CARBOXAMIDES AS ANALGESIC AND ANTI-INFLAMMATORY AGENTS

CROSS-REFERENCE TO RELATED APPLICATION

This application is a continuation-in-part of application Ser. No. 590,659, filed Mar. 19, 1984, now abandoned.

BACKGROUND OF THE INVENTION

This application relates to new chemical compounds which are of value as new medicinal agents. More particularly the new chemical compounds are derivatives of 2-oxindole-1-carboxamide, and they are further substituted at the 3-position by an acyl group. These new chemical compounds are inhibitors of both the cyclooxygenase (CO) and lipoxygenase (LO) enzymes.

The compounds of this invention are useful as analgesic agents in mammals, particularly man, and they are of use in ameliorating or eliminating pain, such as the pain experienced by patients recovering from surgery or trauma.

In addition to their usefulness for acute administration to combat pain, the compounds of this invention are useful for chronic administration to mammals, particularly man, to alleviate the symptoms of chronic diseases, such as the inflammation and pain associated with rheumatoid arthritis and osteoarthritis.

SUMMARY OF THE INVENTION

This invention provides novel 2-oxindole-1-carboxamide compounds of the formula

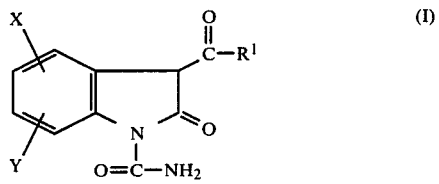

and the pharmaceutically-acceptable base salts thereof; wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7-ethylenedioxy group;

or X and Y when taken together and when attached to adjacent carbon atoms, form a divalent radical Z, wherein Z is selected from the group consisting of

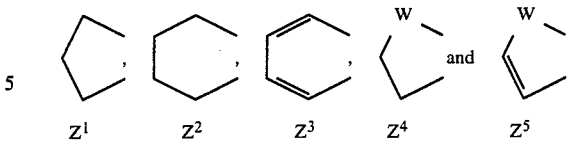

wherein W is oxygen or sulfur;

$R^1$ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)-alkyl having 1 to 3 carbons in said alkyl, naphthyl, bicyclo[2.2.1]heptan-2-yl, bicyclo[2.2.1]hept-5-en-2-yl and $-(CH_2)_n-Q-R°$;

wherein the substituent on said substituted phenyl, said (substituted phenyl)alkyl and said (substituted phenoxy)alkyl is selected from the group consisting of fluoro, chloro, bromo, alkyl having 1 to 4 carbons, alkoxy having 1 to 4 carbons and trifluoromethyl; n is zero, 1 or 2; Q is a divalent radical derived from a compound selected from the group consisting of furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b]thiophene; and R° is hydrogen or alkyl having 1 to 3 carbons.

Said compounds of formula I are active as analgesic agents, and as agents for treating inflammatory diseases, such as the arthritides. Accordingly this invention provides a method of eliciting an analgesic response in a mammalian subject, especially man; a method of treating an inflammatory disease in a mammalian subject, especially man; and pharmaceutical compositions comprising a compound of formula I and a pharmaceutically-acceptable carrier.

A first preferred group of compounds of this invention consists of the compounds of formula I, wherein Y is hydrogen and X is selected from the group consisting of 5-chloro, 6-chloro, 5-fluoro, 6-fluoro, 5-trifluoromethyl and 6-trifluoromethyl. Within this first preferred group, particularly preferred compounds are those wherein $R^1$ is benzyl, 2-furyl, 2-thienyl, (2-furyl)methyl or (2-thienyl)methyl.

A second preferred group of compounds of this invention consists of the compounds of the formula I, wherein X is selected from the group consisting of 5-chloro and 5-fluoro and Y is selected from the group consisting of 6-chloro and 6-fluoro. Within this second preferred group, particularly preferred compounds are those wherein $R^1$ is benzyl, 2-furyl, 2-thienyl, (2-furyl)methyl or (2-thienyl)methyl.

Especially preferred individual compounds of the invention are:

5-chloro-3-(2-thenoyl)-2-oxindole-1-carboxamide (I: X is 5-chloro; Y is hydrogen; and $R^1$ is 2-thienyl);

5-trifluoromethyl-3-(2-[2-thienyl]acetyl)-2-oxindole-1-carboxamide (I: X is 5-trifluoromethyl; Y is hydrogen; and $R^1$ is 2-[2-thienyl]acetyl);

6-fluoro-3-(2-phenylacetyl)-2-oxindole-1-carboxamide (I: X is 6-fluoro; Y is hydrogen; and $R^1$ is benzyl);

6-chloro-5-fluoro-3-(2-phenylacetyl)-2-oxindole-1-carboxamide (I: X is 5-fluoro; Y is 6-chloro; and $R^1$ is benzyl);

5,6-difluoro-3-(2-furoyl)-2-oxindole-1-carboxamide (I: X is 5-fluoro; Y is 6-fluoro; and $R^1$ is 2-furyl); and 5,6-difluoro-3-(2-thenoyl)-2-oxindole-1-carboxamide (I: X is 5-fluoro; Y is 6-fluoro; $R^1$ is 2-thienyl).

Yet further this invention provides novel compounds of the formula

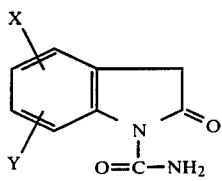

wherein X and Y are as defined previously. The compounds of formula II are useful as intermediates to the compounds of formula I.

DETAILED DESCRIPTION OF THE INVENTION

The analgesic and antiinflammatory compounds of this invention are the compounds of formula I, wherein X, Y and $R^1$ are as defined previously. Thus, the compounds of this invention are derivatives of 2-oxindole, the bicyclic amide of the formula

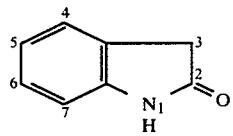

More particularly, the analgesic and antiinflammatory agents of this invention have a carboxamide substituent, —C(=O)—NH$_2$, at the 1-position and an acyl substituent, —C(=O)—$R^1$, at the 3-position of 2-oxindole, and the benzo ring can be further substituted by X and Y groups. X and Y can be certain monovalent substituents as defined previously, or X and Y when on adjacent carbon atoms on the benzo ring can represent a methylenedioxy group, —OCH$_2$O—, or an ethylenedioxy group, —OCH$_2$CH$_2$O—. Yet further, X and Y, when they are attached to adjacent carbon atoms of the benzo ring of the 2-oxindole, can form a divalent unit, Z, such that when Z is taken with the carbon atoms to which it is attached it forms a fused carbocyclic or heterocyclic ring. Certain divalent groups for Z (i.e. $Z^1$-$Z^5$) have been listed earlier. Thus, when Z is $Z^1$, X and Y when taken with the carbons to which they are attached represent a fused cyclopentene ring; and when Z is $Z^5$, X and Y when taken with the carbons to which they are attached represent a fused furan or thiophene ring. Moreover, it is to be understood that when Z is $Z^4$ or $Z^5$, the Z group can be attached in either of two possible ways. Thus, for example, when X and Y are at C-5 and C-6 and they are $Z^5$, the formula I embraces both of the following formulae:

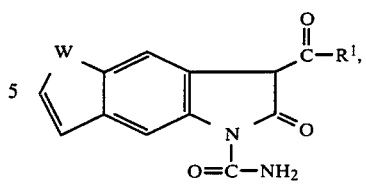

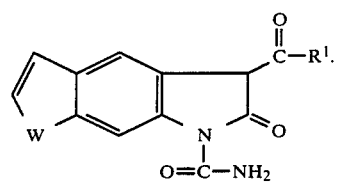

Additionally, as will be appreciated by one skilled in the art, the analgesic and anti-inflammatory compounds of this invention of formula I, wherein X, Y and $R^1$ are defined previously, are capable of enolization, and therefore they can exist in one or more tautomeric (enolic) forms. All such tautomeric (enolic) forms of the compounds of formula I are considered to be within the scope of this invention.

The compounds of formula I are prepared from the appropriate 2-oxindole-1-carboxamide compound of the formula

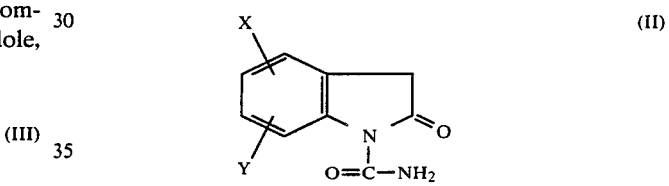

wherein X and Y are as previously defined. This is accomplished by attaching the substituent —C(=O)—$R^1$ to the 3-position of the 2-oxindole nucleus.

The —C(=O)—$R^1$ substituent is attached by reacting a compound of the formula II with an activated derivative of a carboxylic acid of the formula $R^1$—C(=O)OH. The reaction is carried out by treating said compound of formula II in an inert solvent with one molar equivalent, or a slight excess, of an activated derivative of a compound of formula $R^1$—C(=O)OH, in the presence of from one to four equivalents of a basic agent. An inert solvent is one which will dissolve at least one of the reactants, and will not adversely interact with either of the reactants or the product. However, in practice, a polar, aprotic solvent, such as N,N-dimethylformamide, N,N-dimethylacetamide, N-methylpyrrolidone or dimethyl sulfoxide, is commonly used. Conventional methods for activating the acid of formula $R^1$—C(=O)OH are used. For example, acid halides, e.g., acid chlorides, symmetrical acid anhydrides, $R^1$—C(=O)—O—C(=O)—$R^1$, mixed acid anhydrides with a hindered low-molecular weight carboxylic acid, $R^1$—C(=O)—O—C(=O)—$R^3$, where $R^3$ is a bulky lower-alkyl group such as t-butyl, and mixed carboxylic-carbonic anhydrides, $R^1$—C(=O)—O—C(=O)—$OR^4$, wherein $R^4$ is a low-molecular weight alkyl group, can all be used. In addition, N-hydroxyimide esters (such as N-hydroxysuccinimide and N-hydroxyphthalimide esters), 4-nitrophenyl esters, thiol esters (such as thiol phenyl esters) and 2,4,5-trichlorophenyl esters, and the like, can be used. Moreover, in those cases in which $R^1$ is a heteroaryl group (e.g., furyl), simple alkyl esters of the formula $R^1$—C(=O)—O—$R^4$, where $R^4$ is a low-molecular weight alkyl group (e.g., ethyl), can sometimes be used as the activated derivative of the acid of formula $R^1$—C(=O)—OH when attaching the —C(=O)—$R^1$ substituent to the 3-position of the 2-oxindole compound of formula II.

A wide variety of basic agents can be used in the reaction between a compound of formula II and the activated derivative of the acid of the formula $R^1$—C(=O)OH. However, preferred basic agents are tertiary amines, such as trimethylamine, triethylamine, tributylamine, N-methylmorpholine, N-methylpiperidine and 4-(N,N-dimethylamino)pyridine.

The reaction between a compound of the formula II and the activated derivative of the acid of formula $R^1$—C(=O)—OH is usually carried out in the temperature range from $-10°$ to $25°$ C. Reaction times of from 30 minutes to a few hours are common. At the end of the reaction, the reaction medium is usually diluted with water and acidified, and then the product can be recovered by filtration. It can be purified by standard methods, such as recrystallization.

The 2-oxindole-1-carboxamide compounds of the formula II can be prepared by two methods. In the first method, a 2-(2-ureidophenyl)acetic acid compound of the formula IV is cyclized by treatment with trifluoroacetic acid and trifluoroacetic anhydride, viz:

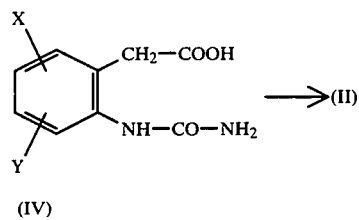

(IV)

wherein X and Y are as defined previously. In general, a solution of a compound of the formula IV in trifluoroacetic acid is treated with from 2 to 5 molar equivalents, and preferably about 3 molar equivalents, of trifluoroacetic anhydride, and the resulting solution is heated at reflux for 0.5 to 3 hours, and usually about 1 hour. Removal of the solvents then provides the compound of the formula II. The compound of formula II can be purified by standard techniques such as recrystallization, if desired. Alternatively it can be used directly to form a compound of the formula I.

The compounds of the formula IV can be prepared by basic hydrolysis of a compound of the formula V:

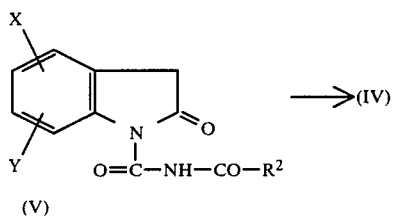

(V)

wherein X and Y are as defined previously and $R^2$ is a lower-alkyl group or lower-cycloalkyl group. Particularly useful groups for $R^2$ are isobutyl and cyclohexyl groups.

The basic hydrolysis of a compound of the formula V, wherein $R^2$ is isobutyl or cyclohexyl, is normally carried out by treating a compound of formula V with a large excess of dilute aqueous potassium hydroxide solution (e.g., 0.5N to 3.0N, usually 1.0N) at about room temperature or slightly above. The reaction usually takes place relatively rapidly and it is usually complete within 1 to 2 hours. The reaction mixture is then acidified (HCl) and the product is then isolated by filtration or by solvent extraction using a volatile, water-immiscible, organic solvent. The compound of formula IV can be purified, for example, by recrystallization, if desired, or it can be cyclized directly to a 2-oxindole-1-carboxamide of formula II.

The compounds of formula V are prepared by reaction of the appropriate 2-oxindole of the formula VI with an acyl isocyanate of the formula $R^2$—C(=O)—N=C=O:

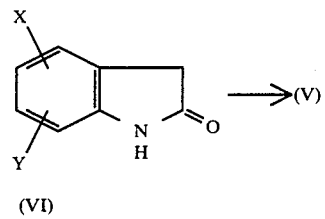

(VI)

The conversion of VI to V can be carried out by heating substantially equimolar amounts of the two reactants in refluxing toluene for a few hours, e.g., 2 hours.

In the second method for preparing the 2-oxindole-1-carboxamide compounds of the formula II, a 2-oxindole of the formula VI is reacted with chlorosulfonyl isocyanate to give the intermediate N-chlorosulfonyl-2-oxindole-1-carboxamide of formula VII, followed by removal of the chlorosulfonyl group by hydrolysis, viz.,

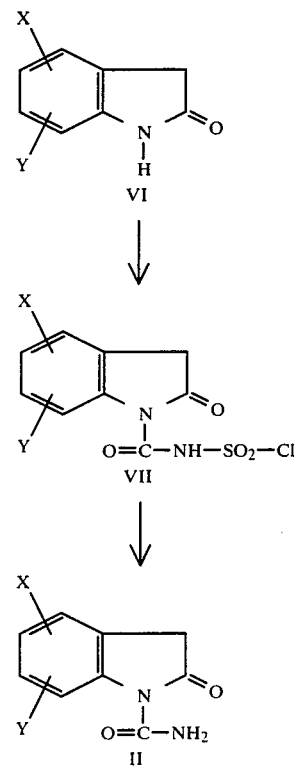

The first step of the sequence, reaction of the appropriate 2-oxindole compound of the formula VI with chlorosulfonyl isocyanate, is conducted in a reaction-inert solvent medium; i.e., a solvent which does not react with the chlorosulfonyl isocyanate or the N-chlorosulfonyl-2-oxindole-1-carboxamide product of formula VII. Said solvent need not bring about complete solution of the reactants. Representative solvents are dialkyl ethers such as diethyl ether; cyclic ethers such as dioxane and tetrahydrofuran; aromatic hydrocarbons such as benzene, xylene and toluene; chlorinated hydrocarbons such as methylene chloride and chloroform; acetonitrile; and mixtures thereof.

The reaction is generally conducted at temperatures ranging from ambient temperature (about 20° C.) to the reflux temperature of the solvent used. In general, temperatures of from 25° C. to 110° C. are favored. Temperatures below 20° C., e.g., down to −70° C., can be used if desired. However, temperatures below 0° C. are avoided, if practical, from the standpoint of yield of desired product for reasons of economy.

The 2-oxindole compound of formula VI and chlorosulfonyl isocyanate are generally reacted in molar proportions ranging from equimolar to 30% excess of chlorosulfonyl isocyanate, i.e., 1:1 to 1:1.3. Larger excesses of chlorosulfonyl isocyanate appear to afford no advantages and are not used for reasons of economy.

The chlorosulfonyl derivatives of formula VII thus produced can be isolated, if desired, or can be converted directly in the same reaction vessel without isolation to a compound of formula II. Isolation of the intermediate chlorosulfonyl compounds of formula VII is achieved by procedures known to those skilled in the art, e.g., by filtration or by evaporation of the solvent.

The hydrolysis of the chlorosulfonyl derivatives of formula VII is carried out by treating the formula VII compounds, with or without isolation thereof, with water, aqueous acid or aqueous base. Water alone or aqueous acid are generally favored as the hydrolyzing agent, even in instances wherein the hydrolysis step involves a two-phase system. The rate of hydrolysis is sufficiently rapid as to overcome any solubility problems of the reactants. However, from the standpoint of large scale reactions, the use of water alone is more economical than are the other hydrolysis methods.

The use of an aqueous organic acid as hydrolyzing agent sometimes overcomes the development of two-phase reaction systems. This is often the case when aqueous acetic acid is used. The amount of acid is not critical to the hydrolysis step. It can range from less than equimolar quantities to greater than equimolar quantities. Also not critical is the concentration of the acid used. In general, when aqueous acid is used for the hydrolysis step, from about 0.1 mole of acid per mole of compound of formula VII to up to 3 moles of acid per mole of compound of formula VII are used. Acid concentrations of from about 1 molar to 6 molar are generally used for ease of handling. The use of aqueous acid is often resorted to when the intermediate of formula VII is isolated and a single-phase hydrolysis mixture is desired. Representative acids are hydrochloric, sulfuric, nitric, phosphoric, acetic, formic, citric and benzoic acids.

In an alternate method, the compounds of formula I can also be prepared by reaction of a compound of formula VIII with chlorosulfonyl isocyanate, followed by hydrolysis:

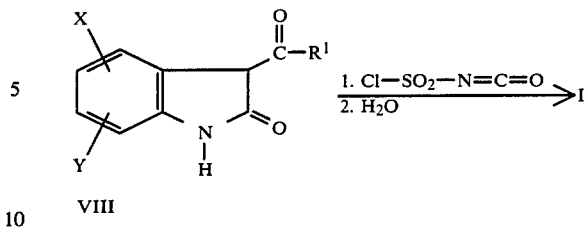

VIII wherein X, Y and $R^1$ are as previously defined. The reaction of the compound of formula VIII with chlorosulfonyl isocyanate, and the subsequent hydrolysis step, are carried out in the same manner as described earlier for the conversion of the 2-oxindole compound of formula VI into the chlorosulfonyl compound of formula VII, and its subsequent hydrolysis to give the compound of formula II.

The compounds of formula VIII are prepared by attachment of the —C(=O)—$R^1$ substituent to the 3-position of the requisite 2-oxindole compound of formula VI. This acylation reaction is carried out by reacting a compound of the formula VI with a derivative of the appropriate acid of the formula $R^1$—C(=O)—OH, in a lower-alkanol solvent (e.g. ethanol), in the presence of an alkali metal salt of the lower-alkanol solvent (e.g. sodium ethoxide), according to standard procedures. Typical derivatives of the acid of the formula $R^1$—C(=O)OH which can be used include acid chlorides, acid anhydrides of the formula $R^1$—C(=O)—O—C(=O)—$R^1$, $R^1$—C(=O)—O—C(=O)—$R^3$ and $R^1$—C(=O)—O—C(=O)—$OR^4$, and simple alkyl esters of the formula $R^1$—C(=O)—$OR^4$, wherein $R^3$ and $R^4$ are as defined previously. Usually, a small excess of the derivative of the acid of formula $R^1$—C(=O)—OH is used, and the alkoxide salt is usually present in an amount from one to two molar equivalents, based on said derivatives of the acid of formula $R^1$—C(=O)OH. The reaction between the derivative of the acid of the formula $R^1$—C(=O)OH and the compound of formula VI is usually started at 0° to 25° C., but it is then usual to heat the reaction mixture at a temperature in the range from 50° to 130° C., and preferably at about 80° C., to complete the reaction. Under these circumstances, reaction times of a few hours, e.g. two hours, up to a few days, e.g., two days, are commonly used. The reaction mixture is then cooled, diluted with an excess of water, and acidified. The product of formula VIII can then be recovered by filtration or by the standard procedure of solvent extraction.

Some of the 2-oxindole-1-carboxamide compounds of the formula II can be prepared conveniently from other compounds of the formula II, by conversion of one X or Y substituent into a different X or Y substituent. For example, compounds of the formula II, in which X is alkylsulfinyl or alkylsulfonyl, can be prepared from the appropriate compound of formula II, in which X is alkylthio, by oxidation. This oxidation can be carried out by standard methods, e.g. using a peroxycarboxylic acid such as 3-chloroperbenzoic acid. For conversion of alkylthio into alkylsulfinyl, 1.0 to 1.2 molar equivalents of oxidant is used; for conversion of alkylthio into alkylsulfonyl, 2.0 to 2.4 molar equivalents of oxidant is used. Additionally, compounds of the formula II, in which X is alkanamido or benzamido, can be prepared by acylation of the corresponding compound in which X is amino. This can be carried out by acylation with an alkanoyl chloride or benzoyl chloride, according to standard procedures.

The 2-oxindole compounds of formula VI are prepared by known methods, or methods analogous to known methods. Consult: "Rodd's Chemistry of Carbon Compounds," Second Edition, S. Coffey editor, Volume IV Part A, Elsevier Scientific Publishing Company, 1973, pp. 448–450; Gassman et al., *Journal of Organic Chemistry,* 42, 1340 (1977); Wright et al., *Journal of the American Chemical Society,* 78, 221 (1956); Beckett et al., *Tetrahedron,* 24, 6093 (1968); U.S. Pat. Nos. 3,882,236, 4,006,161 and 4,160,032; Walker, *Journal of the American Chemical Society,* 77, 3844 (1955); Protiva et al., *Collection of Czechoslovakian Chemical Communications,* 44, 2108 (1979); McEvoy et al., *Journal of Organic Chemistry,* 38, 3350 (1973); Simet, *Journal of Organic Chemistry,* 28, 3580 (1963); Wieland et al., *Chemische Berichte,* 96, 253 (1963); and references cited therein.

The compounds of the formula I are acidic and they form base salts. All such base salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate, or by interconverting one salt with another salt. The salts are recovered either by filtration, by precipitation with a non-solvent followed by filtration, by evaporation of the solvent, as appropriate, or, in the case of aqueous solutions, by lyophilization. Typical salts of the compounds of formula I which can be prepared are primary, secondary and tertiary amine salts, alkali metal salts and alkaline earth metal salts. Especially valuable are the sodium, potassium, ammonium, ethanolamine, diethanolamine and triethanolamine salts.

Basic agents suitably employed in salt formation belong to both the organic and inorganic types, and they include ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are: ammonia; primary amines, such as n-propylamine, n-butylamine, aniline, cyclohexylamine, benzylamine, p-toluidine, ethanolamine and glucamine; secondary amines, such as diethylamine, diethanolamine, N-methylglucamine, N-methylaniline, morpholine, pyrrolidine and piperidine; tertiary amines, such as triethylamine, triethanolamine, N,N-dimethylaniline, N-ethylpiperidine and N-methylmorpholine; hydroxides, such as sodium hydroxide; alkoxides, such as sodium ethoxide and potassium methoxide; hydrides, such as calcium hydride and sodium hydride; and carbonates, such as potassium carbonate and sodium carbonate.

Also embraced by this invention are the solvates, e.g. hydrates such as hemihydrates and monohydrates, of the analgesic and antiinflammatory compounds of the formula I.

The compounds of formula I possess analgesic activity. This activity has been demonstrated in mice by showing blockade of the abdominal stretching induced by administration of 2-phenyl-1,4-benzoquinone (PBQ). The method used was based on that of Siegmund et al., *Proc. Soc. Exp. Biol. Med.,* 95, 729–731, (1957), as adapted for high throughput [see further Milne and Twomey, *Agents and Actions,* 10, 31–37, (1980)]. The mice used in these experiments were Carworth males, albino CF-1 strain, weighing 18–20 g. All mice were fasted overnight prior to drug administration and testing.

The compounds of formula I were dissolved or suspended in a vehicle consisting of ethanol (5%), emulphor 620 (a mixture of polyoxyethylene fatty acid esters, 5%) and saline (90%). This vehicle also served as control. Doses were on a logarithmic scale (i.e., . . . 0.32, 1.0, 3.2, 10, 32 . . . mg/kg), and were calculated from weights of the salt when applicable, and not of the acid. The route of administration was oral, with concentrations varied to allow a constant dosage of 10 ml/kg of mouse. The aforesaid method of Milne and Towney was used to determine efficacy and potency. Mice were treated with compounds orally, and one hour later received PBQ, 2 mg/kg intraperitoneally. Individual mice were then immediately placed in a warmed lucite chamber, and, starting five minutes after PBQ administration, the number of abdominal constrictions during the subsequent 5 minutes was recorded. The degree of analgesic protection (% MPE) was calculated on the basis of suppression of abdominal constriction relative to counts from concurrent control animals run on the same day. At least four such determinations (N≧5) provided dose-response data for generation of an MPE$_{50}$, the best estimate of the dose that reduces abdominal constriction to 50% of control levels.

The compounds of formula I also possess anti-inflammatory activity. This activity has been demonstrated in rats by a method based on the standard carrageenin-induced rat-foot edema test. [Winter et al., *Proc. Soc. Exp. Biol. Med.,* 111, 544, (1963)].

Unanesthetized, adult, male, albino rats of 150 g to 190 g body weight were numbered, weighed, and an ink mark placed on the right lateral malleolus. Each paw was immersed in mercury exactly to the ink mark. The mercury was contained in a glass cylinder, connected to a Statham Pressure Transducer. The output from the transducer was fed through a control unit to a microvoltameter. The volume of mercury displaced by the immersed paw was read. Drugs were given by gavage. One hour after drug administration, edema was induced by injection of 0.05 ml of 1% solution of carrageenin into the plantar tissue of the marked paws. Immediately thereafter, the volume of the injected foot was measured. The increase in foot volume 3 hours after the injection of carrageenin constitutes the individual inflammatory response.

The analgesic activity of the compounds of formula I makes them useful for acute administration to mammals for the control of pain, e.g., post-operative pain and the pain of trauma. Additionally the compounds of formula I are useful for chronic administration to mammals for the alleviation of the symptoms of chronic diseases, such as the inflammation of rheumatoid arthritis, and the pain associated with osteoarthritis and other musculoskeletal disorders.

When a compound of the formula I or a pharmaceutically acceptable salt thereof is to be used as either an analgesic agent or an anti-inflammatory agent, it can be administered to a mammalian subject either alone, or, preferably, in combination with pharmaceutically-acceptable carriers or diluents in a pharmaceutical composition, according to standard pharmaceutical practice. A compound can be administered orally or parenterally. Parenteral administration includes intravenous, intramuscular, intraperitoneal, subcutaneous and topical administration.

In a pharmaceutical composition comprising a compound of formula I, or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

For oral use of a compound of formula I of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a compound of formula I or salt thereof is used in a human subject, the daily dosage will normally be determined by the prescribing physician. Moreover, the dosage will vary according to the age, weight and response of the individual patient, as well as the severity of the patient's symptoms and the potency of the particular compound being administered. However, for acute administration to relieve pain, an effective dose in most instances will be 0.01 to 0.5 g as needed (e.g., every four to six hours). For chronic administration, in most instances an effective dose will be from 0.01 to 1.0 g per day, and preferably 20 to 250 mg per day, in single or divided doses. On the other hand, it may be necessary to use dosages outside these limits in some cases.

The following examples and preparations are being provided solely for the purpose of further illustration.

EXAMPLE 1

5-Chloro-3-(2-thenoyl)-2-oxindole-1-carboxamide

A stirred slurry of 21.1 g (0.1 mole) of 5-chloro-2-oxindole-1-carboxamide and 26.9 g (0.22 mole) of 4-(N,N-dimethylamino)pyridine in 200 ml of N,N-dimethylformamide was cooled to ice-bath temperature, and then a solution of 16.1 g (0.11 mole) of 2-thenoyl chloride in 50 ml of N,N-dimethylformamide was added dropwise. Stirring was continued for ca. 30 minutes, and then the reaction mixture was poured into a mixture of 1 liter of water and 75 ml of 3N hydrochloric acid. The resulting mixture was cooled in an ice-bath, and then the solid was collected by filtration. The solid was washed with water and then recrystallized from 1800 ml of acetic acid, to give 26.6 g of the title compound as fluffy, yellow crystals, m.p. 230° C. (dec.).

A sample of the title compound from a similar experiment gave the following results on elemental analysis.

Analysis: Calcd. for $C_{14}H_9ClN_2O_3S$: C, 52.42; H, 2.83; N, 8.74%. Found: C, 52.22; H, 2.81; N, 8.53%.

EXAMPLE 2

Reaction of the appropriate 2-oxindole-1-carboxamide with the requisite acid chloride of the formula $R^1$—CO—Cl, substantially according to the procedure of Example 1, afforded the following compounds:

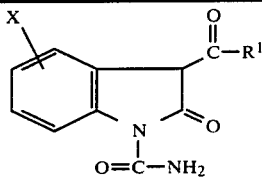

| | | Melting Point (°C.)[1,2] | Analysis | | | | | |
|---|---|---|---|---|---|---|---|---|
| | | | Calculated (%) | | | Found (%) | | |
| X | $R^1$ | | C | H | N | C | H | N |
| 5-Cl | 2-furyl | 234d | 55.18 | 2.98 | 9.20 | 55.06 | 3.09 | 9.32 |
| 5-Cl | 2-(2-thienyl)methyl | 240d[3] | 53.81 | 3.31 | 8.37 | 53.40 | 3.31 | 8.37 |
| 6-Cl | 2-furyl | 218–219 | 55.19 | 2.98 | 9.19 | 54.89 | 2.90 | 9.23 |
| 6-Cl | 2-thienyl | 201–202 | 52.44 | 2.83 | 8.74 | 51.86 | 3.03 | 8.61 |
| 6-Cl | 2-(2-thienyl)methyl | 219–220 | 53.83 | 3.31 | 8.37 | 53.70 | 3.45 | 8.38 |
| 5-F | 2-furyl | 232d | 58.34 | 3.15 | 9.72 | 57.99 | 3.13 | 9.70 |
| 5-F | 2-thienyl | 231d | 55.25 | 2.98 | 9.21 | 55.49 | 3.00 | 9.28 |
| 5-F | 2-(2-thienyl)methyl | 243d | 56.59 | 3.48 | 8.80 | 56.76 | 3.48 | 8.81 |
| 6-F | 2-furyl | 230.5–233.5 | 58.33 | 3.13 | 9.75 | 57.73 | 3.04 | 9.72 |
| 6-F | 2-thienyl | 117.5–120.5 | 55.26 | 2.96 | 9.21 | 55.14 | 2.91 | 9.15 |
| 6-F | 2-(2-thienyl)methyl | 214.5–217 | 56.61 | 3.48 | 8.80 | 55.97 | 3.52 | 8.65 |
| 5-$CF_3$ | 2-furyl | 235.5d | 53.26 | 2.68 | 8.28 | 52.84 | 2.96 | 8.17 |
| 5-$CF_3$ | 2-thienyl | 212.5d | 50.85 | 2.56 | 7.91 | 50.43 | 2.72 | 7.90 |
| 5-$CF_3$ | 2-(2-thienyl)methyl | 223.5d | 52.17 | 3.01 | 7.61 | 51.72 | 3.37 | 7.45 |
| 6-$CF_3$ | 2-furyl | 206–208 | 53.26 | 2.68 | 8.28 | 52.87 | 3.03 | 8.27 |
| 6-$CF_3$ | 2-thienyl | 177–180 | 50.86 | 2.56 | 7.91 | 50.69 | 2.75 | 7.96 |

[1]All compounds were recrystallized from acetic acid unless otherwise noted.
[2]The letter "d" in this column indicates that the compound melted with decomposition.
[3]Recrystallized from N,N—dimethylformamide.

EXAMPLE 3

5-Chloro-3-acetyl-2-oxindole-1-carboxamide

A stirred slurry of 842 mg (4.0 mmole) of 5-chloro-2-oxindole-1-carboxamide and 1.08 g (8.8 mmole) of 4-(N,N-dimethylamino)pyridine in 15 ml of N,N-dimethylformamide was cooled to ice-bath temperature, and then a solution of 449 mg (4.4 mmole) of acetic anhydride in 5 ml of N,N-dimethylformamide was added dropwise. Stirring was continued for ca. 30 minutes, and then the reaction mixture was poured into a mixture of 75 ml of water and 3 ml of 3N hydrochloric acid. The resulting mixture was cooled in an ice-bath and the solid was recovered by filtration. The solid was recrystallized from acetic acid to give 600 mg of fluffy, pale pink crystals, m.p. 237.5° C. (dec.).

Analysis: Calcd. for $C_{11}H_9ClN_2O_3$: C, 52.29; H, 3.59; N, 11.09%. Found: C, 52.08; H, 3.63; N, 11.04%.

EXAMPLE 4

Reaction of the appropriate 2-oxindole-1-carboxamide with an activated derivative of the requisite carboxylic acid of the formula $R^1$—CO—OH, substantially according to the procedure of Example 1 or Example 3, afforded the following compounds:

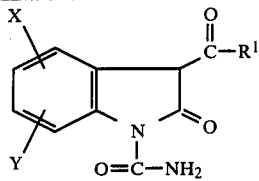

| X | Y | $R^1$ | Melting Point (°C.)[1] |
|---|---|---|---|
| H | H | 2-furyl | 223d |
| H | H | 2-thienyl | 210d |
| H | H | 2-(2-thienyl)methyl | 233d |
| H | H | cyclohexyl | 213d |
| H | H | isopropyl | 205–206 |
| H | H | cyclopropyl | 207.5–208.5 |
| H | H | phenoxymethyl | 187.5d |
| H | H | (4-chlorophenoxy)methyl | 190d |
| H | H | methyl | 200–201.5 |
| 5-Cl | H | cyclohexyl | 210d |
| 5-F | H | phenoxymethyl | 201–202d |
| 5-F | H | isopropyl | 230d |
| 5-F | H | cyclohexyl | 222d |
| 5-Cl | H | isopropyl | 229d |
| 5-Cl | H | cyclopropyl | 243.5d |
| 6-F | H | bicyclo[2.2.1]heptan-2-yl | 111.5–114 |
| 4-Cl | H | 2-thienyl | 165–167d |
| 4-Cl | H | 2-furyl | 183–185d |
| 5-$CH_3$ | 6-F | 2-furyl | 210–215 |
| 6-F | H | methyl | 226.5–229 |
| 5-$OCH_3$ | 6-$OCH_3$ | methyl | 226–230 |
| 5-$OCH_3$ | 6-$OCH_3$ | 2-thienyl | 195–197 |
| 6-Cl | H | cyclohexyl | 225–226 |
| 5-$CF_3$ | H | isopropyl | 203d |
| 5-F | H | cyclopropyl | 228.5d |
| H | H | 4-chlorophenyl | 229d |
| H | H | 4-methylphenyl | 214.5d |
| H | H | benzyl | 226.5d |
| H | H | 1-(phenyl)ethyl | 188.5–189.5 |
| 5-$CF_3$ | H | cyclopropyl | 265d |
| 5-$CF_3$ | H | cyclohexyl | 185–186 |
| 5-$CF_3$ | H | methyl | 225d |
| 5-$CF_3$ | H | phenyl | 221.5d |
| 5-$CF_3$ | H | 4-chlorophenyl | 225d |
| 5-$CF_3$ | H | 4-methylphenyl | 224d |
| 6-$CF_3$ | H | isopropyl | 199–202 |
| 6-$CF_3$ | H | bicyclo[2.2.1]heptan-2-yl | 192–198 |
| 6-$SCH_3$ | H | (2-thienyl)methyl | 214–215 |
| 4-$SCH_3$ | H | bicyclo[2.2.1]heptan-2-yl | 200–202 |
| 6-F | H | isopropyl | 188–191 |
| 6-$SCH_3$ | H | bicyclo[2.2.1]heptan-2-yl | 218.5–220.5 |
| 5-$CF_3$ | H | benzyl | 217d |
| 5-$CF_3$ | H | 1-(phenyl)ethyl | 208d |
| 5-$CF_3$ | H | phenoxymethyl | 205.5–206.5d |
| 5-$CH_3$ | 6-$CH_3$ | 2-furyl | 220d |
| 4-$CH_3$ | 5-$CH_3$ | 2-furyl | 191d |
| 5-$CH_3$ | 6-$CH_3$ | 2-thienyl | 197d |
| 4-$CH_3$ | 5-$CH_3$ | 2-thienyl | 205d |
| 5-$CH_3$ | 6-$CH_3$ | (2-thienyl)methyl | 231d |
| 5-Cl | H | phenyl | 232.5d |
| 5-Cl | H | 4-chlorophenyl | 242d |
| 5-Cl | H | 4-methylphenyl | 231d |
| 5-Cl | H | benzyl | 244.5d |
| 6-Cl | H | benzyl | 229–230d |
| 4-Cl | H | cyclohexyl | 188–189 |
| 4-Cl | H | isopropyl | 158–160 |
| 4-$SCH_3$ | H | 2-furyl | 203–206 |
| 6-Br | H | bicyclo[2.2.1]heptan-2-yl | 232–235 |
| 5-$CH_3$ | H | (2-thienyl)methyl | 243–244d |
| 6-Cl | H | 4-chlorophenyl | 220–222 |
| 5-$CH_3$ | H | phenyl | 215–216.5d |
| 5-$OCH_3$ | H | 4-chlorophenyl | 238–240d |
| 5-$OCH_3$ | H | phenyl | 209–210d |
| 5-$CH_3$ | H | cyclohexyl | 219–220d |
| 4-Cl | H | methyl | 184d |
| 5-$OCH_3$ | H | isopropyl | 194–195 |
| 5-$OCH_3$ | H | cyclohexyl | 221–222 |
| 5-$CH_3$ | H | methyl | 223–224d |
| 5-Cl | H | cyclopentyl | 214–215d |
| 5-Cl | H | cyclobutyl | 214–215d |
| 5-$CF_3$ | H | cyclopentyl | 188–189 |
| 6-Cl | H | cyclobutyl | 227d |
| 6-Cl | H | cyclopentyl | 224–225.5d |
| 5-Cl | H | 1-phenylethyl | 206d |
| 5-Cl | H | phenoxymethyl | 218d |
| 5-F | H | bicyclo[2.2.1]heptan-2-yl | 216d |
| 5-$CF_3$ | H | bicyclo[2.2.1]heptan-2-yl | 212d |
| 6-Br | H | 2-furyl | 234–237 |
| 6-Cl | H | 1-(phenyl)ethyl | 222–223d |
| 5-$NO_2$ | H | 2-thienyl | 220.5–225 |
| 5-$NO_2$ | H | benzyl | 232–236 |
| 5-$OCH_3$ | H | 1-(phenyl)ethyl | 204–205.5 |
| 5-$OCH_3$ | H | 2-thienyl | 188–189d |
| 6-Cl | H | phenyl | 236–237d |
| 5-$CH_3$ | H | 4-chlorophenyl | 247–248d |
| H | H | 2-pyrrolyl | 214–215d |
| 5-Cl | H | 2-pyrrolyl | 217–218d |
| 5-F | H | 3-thienyl | 236.5d |
| 5-Cl | H | 3-thienyl | 238d |
| 5-F | H | 3-furyl | 229.5d |
| 5-Cl | H | 3-furyl | 231.5d |
| 6-Cl | H | 3-furyl | 223.5d |
| 5-$CF_3$ | H | 3-furyl | 214d |
| 5-F | H | (3-thienyl)methyl | 239.5d |
| 5-Cl | H | (3-thienyl)methyl | 237d |
| 6-Cl | H | (3-thienyl)methyl | 220.5d |
| 5-$CF_3$ | H | (3-thienyl)methyl | 210.5d |
| 5-Cl | 6-Cl | 2-thienyl | 227d |
| 5-Cl | 6-Cl | (2-thienyl)methyl | 243d |
| 6-$C_6H_5$ | H | 2-thienyl | 212d |
| 6-$C_6H_5$ | H | (2-thienyl)methyl | 215d |
| H | H | 2,4-dichlorophenyl | 221d |
| 5-Cl | H | trifluoromethyl | 224–225d |
| 5-$CH_3$ | H | 2-furyl | 214–215d |
| 5-$CH_3$ | H | benzyl | 249–250d |
| 5-$CH_3$ | H | 2-thienyl | 221–222d |
| 5-$OCH_3$ | H | (2-thienyl)methyl | 239–242d |
| 5-Cl | H | bicyclo[2.2.1]heptan-2-yl | 219–221d |
| 5-$CF_3$ | H | trifluoromethyl | 217–219d |
| 5-$OCH_3$ | H | benzyl | 240–241d |
| 5-$OCH_3$ | H | methyl | 233–234d |
| 5-$CF_3$ | H | 3-thienyl | 225d |
| 6-Cl | H | (3-thienyl)methyl | 220.5d |
| H | H | 5-pyrimidinyl | 238–240d |
| 5-Cl | H | bicyclo[2.2.1]hept-en-5-yl | 211.5d |
| H | H | bicyclo[2.2.1]hept-2-en- | 210.5d |

-continued

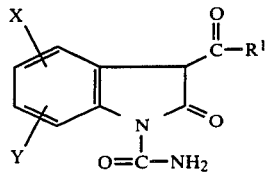

| X | Y | R[1] | Melting Point (°C.)[1] |
|---|---|---|---|
| 6-Cl | H | bicyclo[2.2.1]hept-2-en-5-yl | 219d |
| 5-Cl | H | 1-phenylethyl | 192–193[2] |
| 5-CF$_3$ | H | 1-phenylethyl | 169.5–170.5[3] |
| 5-Cl | H | 1-phenylethyl | 193–194[4] |
| 5-CF$_3$ | H | 1-phenylethyl | 172–173[5] |
| 5-CF$_3$ | H | 3-trifluoromethylbenzyl | 153–155d |
| 6-Cl | H | 3-trifluoromethylbenzyl | 200–202d |
| H | H | 2-chlorobenzyl | 236d |
| 5-Cl | H | 2-chlorobenzyl | 237.5d |
| 5-F | H | 2-chlorobenzyl | 231d |
| 5-CF$_3$ | H | 2-chlorobenzyl | 198.5–199.5 |
| 5-F | H | 3-trifluoromethylbenzyl | 214–215d |
| 6-Cl | H | 3-thienyl | 210–212d |
| 6-Cl | H | 2-chlorobenzyl | 231d |
| 5-Cl | H | 4-chlorobenzyl | 242–243d |
| 6-Cl | H | 4-chlorobenzyl | 195–198d |
| 5-F | H | 4-chlorobenzyl | 232–234d |
| 5-Cl | H | 3-chlorobenzyl | 222–225d |
| 5-F | H | 3-chlorobenzyl | 219–220d |
| H | H | 3-trifluoromethylbenzyl | 235–236d |
| 5-C$_6$H$_5$CO | H | benzyl | 231d |
| 5-C$_6$H$_5$CO | H | (2-thienyl)methyl | 236–238 |
| 5-C$_6$H$_5$CO | H | 2-thienyl | 185–187 |
| 5-CH$_3$CO | H | benzyl | 239–241 |
| 5-C$_4$H$_3$SCO[6] | H | (2-thienyl)methyl | 230–232 |
| 6-F | H | 5-methyl-3-isoxazolyl | 224–226 |
| 5-Cl | H | 5-methyl-3-isoxazolyl | 252–254 |
| 5-CH$_3$CO | H | (2-thienyl)methyl | 226–227 |
| 5-C$_4$H$_3$SCO[6] | H | benzyl | 243–245 |
| 5-F | H | 5-methyl-3-isoxazolyl | 225–226 |
| 5-F | 6-Cl | (2-thienyl)methyl | 228–230 |
| 5-F | 6-Cl | 2-furyl | 250–251 |
| 5-F | 6-Cl | 2-thienyl | 220–221 |
| 5-Cl | H | 1,2,3-thiadiazol-4-yl | 234–238 |
| 6-F | H | 1,2,3-thiadiazol-4-yl | 225–227 |
| 5-F | 6-Cl | benzyl | 243–245 |
| 6-CF$_3$ | H | 1-phenylethyl | 228–231[7] |
| 6-F | H | 1-phenylethyl | 192–194[8] |
| 5-Cl | H | 1-phenoxyethyl | 220–222 |
| 6-F | H | 1-phenoxyethyl | 200–202 |
| 6-F | H | 2-phenylethyl | 149–150.5 |
| 5-Cl | H | 2-phenylethyl | 199–201 |
| 5-F | 6-F | 2-furyl | 240–241.5 |
| 5-F | 6-F | benzyl | 234–237 |
| 5-F | 6-F | (2-thienyl)methyl | 236–238 |
| 5-NO$_2$ | H | 2-furyl | 157–160 |
| 5-NO$_2$ | H | (2-thienyl)methyl | 209–212 |
| 5-Cl | H | 3-trifluoromethylbenzyl | 218–219 |
| 5-NO$_2$ | H | 1-phenylethyl | 208.5–211 |
| 5-Cl | H | (2-furyl)methyl | 233–236 |
| 6-F | H | (2-furyl)methyl | 212–214 |
| 6-F | H | 1,2,5-thiadiazol-3-yl | 237.5–241 |
| 5-Cl | H | 1,2,5-thiadiazol-3-yl | 240.5–243 |
| 6-CF$_3$ | H | 1-phenylethyl | 235–237[9] |
| 6-F | H | 1-phenylethyl | 194–196[10] |
| 6-F | H | 1-phenylethyl | 166–170[11] |
| 6-CF$_3$ | H | 1-phenylethyl | 205–207[11] |
| 6-CF$_3$ | H | (2-thienyl)methyl | 217–218 |
| 5-F | 6-Cl | 2-tetrahydrofuryl | 213.5–215 |
| 5-NO$_2$ | H | 2-tetrahydrofuryl | 216–219 |
| 5-Cl | H | 4-isothiazolyl | 255 |
| 5-Cl | H | 2-thiazolyl | 227 |

-continued

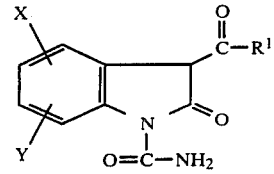

| X | Y | R[1] | Melting Point (°C.)[1] |
|---|---|---|---|
| 5-Cl | H | 1-methyl-5-pyrazolyl | 254 |

[1]The letter "d" in this column indicates that the compound melted with decomposition.
[2]$[alpha]_D^{23} = -300.3°$
[3]$[alpha]_D^{23} = -174.3°$
[4]$[alpha]_D^{23} = +303.8°$
[5]$[alpha]_D^{23} = +169.7°$
[6]5-(2-thenoyl)
[7]$[alpha]_D^{23} = +154.9°$
[8]$[alpha]_D^{23} = +184.9°$
[9]$[alpha]_D^{23} = -170.9°$
[10]$[alpha]_D^{23} = -198.3°$
[11]starting 2-phenylpropionyl chloride was racemic.

EXAMPLE 5

Reaction of 2-thenoyl chloride and 2-furoyl chloride with 5,6-methylenedioxy-2-oxindole-1-carboxamide, using the procedure of Example 1, afforded the following compounds:

5,6-methylenedioxy-3-(2-thenoyl)-2-oxindole-1-carboxamide, m.p. 215°–217° C. (dec) and 5,6-methylenedioxy-3-(2-furoyl)-2-oxindole-1-carboxamide, m.p. 234°–235° C. (dec), respectively.

EXAMPLE 6

By reaction of the appropriate acid chloride of the formula R[1]—CO—Cl with the requisite 2-oxindole-1-carboxamide, using the procedure of Example 1, the following compounds can be prepared.

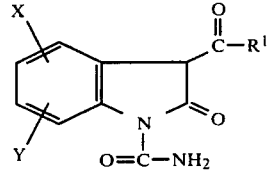

| X | Y | R[1] |
|---|---|---|
| 5-n-OC$_4$H$_9$ | H | 2-furyl |
| 5-OC$_2$H$_5$ | H | 2-thienyl |
| 7-Cl | H | (2-thienyl)methyl |
| 6-F | H | n-hexyl |
| 5-F | H | cycloheptyl |
| 5-Cl | H | 2-fluorophenyl |
| 5-n-C$_4$H$_9$ | H | 2-furyl |
| 5-CH$_3$ | H | 4-bromophenyl |
| 6-SCH$_3$ | H | 3-n-butylphenyl |
| 5-CF$_3$ | H | 3-methoxyphenyl |
| 5-n-SC$_4$H$_9$ | H | 4-isobutoxyphenyl |
| 5-CH$_3$ | 6-CH$_3$ | 3-(phenyl)propyl |
| 6-OCH$_3$ | H | 3-(phenoxy)propyl |
| 6-SCH$_3$ | H | 2-thienyl |
| 5-NO$_2$ | H | (3-fluorophenoxy)methyl |
| H | H | cyclobut-1-en-1-yl |
| 5-Cl | H | cyclohept-1-en-1-yl |
| 6-F | H | (thiophenoxy)methyl |
| 5-CF$_3$ | H | 3-(thiophenoxy)propyl |
| H | H | 1-imidazolyl |
| 5-Cl | 6-Cl | 2-tetrahydropyranyl |
| 6-n-SC$_4$H$_9$ | H | (4-chlorophenoxy)methyl |
| 5-OCH$_3$ | 6-OCH$_3$ | (2-thienyl)methyl |
| 5-Cl | H | (2-furyl)methyl |

-continued

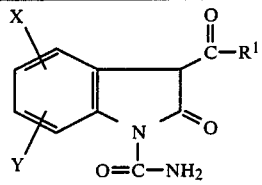

| X | Y | R¹ |
|---|---|---|
| 5-F | 6-Cl | (4-bromophenoxy)methyl |
| 5-F | 6-Cl | 2-tetrahydrothiopyranyl |
| 6-Cl | H | (2-methylphenoxy)methyl |
| 6-Br | H | (4-isobutylphenoxy)methyl |
| 6-n-SC$_4$H$_9$ | H | 2-thienyl |
| 7-Cl | H | (3-methoxyphenoxy)methyl |
| 4-SCH$_3$ | H | (4-butoxyphenoxy)methyl |
| 5-NO$_2$ | H | 3-furyl |
| 4-CH$_3$ | 5-CH$_3$ | 3-thienyl |
| 6-SCH$_3$ | H | 3-methyl-2-furyl |
| 7-Cl | H | 5-propyl-2-furyl |
| 5-CH(CH$_3$)$_2$ | H | 3-methyl-2-thienyl |
| 5-F | 6-Cl | 5-propyl-2-thienyl |
| 5-NO$_2$ | H | 3-(3-thienyl)propyl |
| 5-OC$_2$H$_5$ | H | 1-(2-furyl)ethyl |
| 7-Cl | H | 3-(2-furyl)propyl |
| 6-CH$_3$SO | H | 2-thienyl |
| 6-n-C$_4$H$_9$SO | H | 2-furyl |
| 4-CH$_3$SO$_2$ | H | 3-fluorophenyl |
| 6-n-C$_4$H$_9$SO$_2$ | H | 2-thiazolyl |
| 5-NO$_2$ | H | 2-(3-thienyl)ethyl |
| 6-C$_6$H$_5$ | H | 4-chlorophenyl |
| H | 5-Br | 2-(2-tolyl)ethyl |
| 5-CH$_3$CO | H | 4-trifluoromethylphenyl |
| 6-n-C$_3$H$_7$CO | H | 4-isothiazolyl |
| 5-Cl | H | 1-naphthyl |
| 5-C$_6$H$_5$CO | H | 1,2,3-thiadiazol-4-yl |
| 5-C$_4$H$_3$SCO¹ | H | 3-(3-chlorophenyl)propyl |
| 6-CF$_3$ | H | (4-thiazolyl)methyl |
| 6-F | H | 1,2,5-thiadiazol-3-yl |
| 5-CH$_3$CONH | H | 1-methyl-1-phenylethyl |
| 5-Cl | 6-Cl | 5-methyl-4-isoxazolyl |
| 5-(CH$_3$)$_2$CH—CONH | H | 2-(4-isopropylphenyl)ethyl |
| 5-C$_6$H$_5$CONH | H | 2-thienyl |
| 5-CH$_3$ | 6-CH$_3$ | 4-isopropoxyphenyl |
| 5-SO$_2$N(CH$_3$)$_2$ | H | benzyl |
| 5-F | 6-F | 4-chlorophenoxy |
| 5-SO$_2$N(n-C$_3$H$_7$)$_2$ | H | 2-tetrahydrofuryl |
| H | 4-Cl | 4-pyridyl |
| 6-Cl | H | 3-tetrahydrothienyl |
| H | H | 5-pyrimidyl |
| 5-CH$_3$ | 6-F | 2-pyrazinyl |
| H | H | 2-n-propyl-4-thiazolyl |
| 5-Br | H | 2-oxazolyl |
| H | H | 3-isoxazolyl |
| H | H | 1,3,4-thiadiazol-2-yl |

¹5-(2-thenoyl)

EXAMPLE 7

By reaction of the appropriate acid chloride with the requisite 2-oxindole-1-carboxamide, using the procedure of Example 1, the following compounds can be prepared:

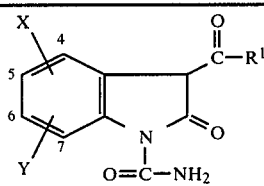

| X and Y* | R¹ |
|---|---|
| 4-CH$_2$—CH$_2$—CH$_2$—5 | 2-furyl |
| 5-CH$_2$—CH$_2$—CH$_2$—6 | 2-thienyl |

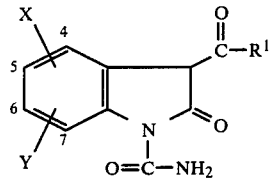

| X and Y* | R¹ |
|---|---|
| 6-CH$_2$—CH$_2$—CH$_2$—CH$_2$—7 | 2-furyl |
| 5-CH=CH—CH=CH—6 | (2-thienyl)methyl |
| 5-O—CH$_2$—CH$_2$—6 | 2-thienyl |
| 5-CH$_2$—CH$_2$—O—6 | 2-furyl |
| 5-S—CH$_2$—CH$_2$—6 | 2-thienyl |
| 5-O—CH=CH—6 | 2-furyl |
| 5-S—CH=CH—6 | (2-thienyl)methyl |
| 5-CH=CH—S—6 | 2-furyl |

*In this column, the numeral to the left of the formula indicates the point attachment of that end of the formula to the 2-oxindole nucleus and the numeral to the right indicates the point of attachment of that end of the formula to the 2-oxindole nucleus.

EXAMPLE 8

5-Chloro-3-(2-thenoyl)-2-oxindole-1-carboxamide

To a stirred solution of 429.9 g (2.04 mole) of 5-chloro-2-oxindole-1-carboxamide in 4 liters of N,N-dimethylformamide was added 547.9g (4.48 mole) of 4-(N,N-dimethylamino)pyridine, and then the mixture was cooled to 8° C. To this mixture was added, with stirring, a solution of 328 g (2.23 mole) of thenoyl chloride in 800 ml N,N-dimethylformamide over a 30 minute period, with the temperature being maintained between 8° and 15° C. Stirring was continued for 30 minutes, and then the reaction mixture was poured with stirring into a mixture of 510 ml of concentrated hydrochloric acid and 12 liters of water. Stirring was continued for 2 hours, and then the solid was collected by filtration and washed with water followed by methanol. The solid was dried to give 675.6 g of the title compound.

A portion (673.5 g, 2.1 mole) of the above title compound was added to 13 liters of methanol and the mixture was heated to reflux. To the refluxing mixture was added 136 g (2.22 mole) of ethanolamine. The resulting solution was cooled to 50° C., 65 g of decolorizing carbon was added, and then the solution was reheated to reflux temperature and maintained there for 1 hour. The hot solution was filtered through supercel (a diatomaceous earth), and the filtrate was cooled to 40° C. To the filtrate was added 392 ml of concentrated hydrochloric acid, slowly, during 30 minutes. The mixture was cooled to 20°-23° C., stirred for 30 minutes, and then the solid was collected by filtration and washed with methanol. The solid was dried, affording 589 g of the title compound, m.p. 229°-231.5° C. (dec.).

EXAMPLE 9

Ethanolamine Salt of 5-Chloro-3-(2-thenoyl)-2-oxindole-1-carboxamide

A slurry of 321 mg (1.0 mmole) of 5-chloro-3-(2-thenoyl)-2-oxindole-1-carboxamide in 25-30 ml of diisopropyl alcohol was heated to boiling, and then a solution of 67 mg of ethanolamine in 1 ml of diisopropyl alcohol was added. This afforded a yellow solution within 2 to 3 minutes. The solution was boiled down to 12-13 ml and then it was allowed to cool. The solid which appeared was recovered by filtration to give 255 mg of the title salt as yellow crystals, m.p. 165.5°–167° C. (slight decomposition).

Analysis: Calcd. for $C_{16}H_{16}ClN_3O_4S$: C, 50.32; H, 4.22; N, 11.00%. Found: C, 50.52; H, 4.44; N, 10.88%.

EXAMPLE 10

Sodium Salt of 5-Chloro-3-(2-thenoyl)-2-oxindole-1-Carboxamide

Part A

To a stirred slurry of 20 g. (62.4 mmole) of 5-chloro-3-(2-thenoyl)-2-oxindole-1-carboxamide in 400 ml. of methanol was added 4.14 ml. (68.6 mmole) of ethanolamine, dropwise, at room temperature. To the clear solution thus obtained, was added a solution of 6.74 g. (124.7 mmole) of sodium methoxide in methanol. The resulting mixture was heated to ca 90° C. and then it was allowed to cool and stirred overnight. The solid which had formed was recovered by filtration and dried at room temperature under high vacuum overnight to give 18.12 g. of crude product. The crude product was recrystallized from methanol-isopropanol to give 1.73 g. of a first crop and 10.36 g. of a second crop of the monohydrate of the sodium salt of 5-chloro-3-(2-thenoyl)-2-oxindole-1-carboxamide. Both crops melted at 236°–238° C.

| | Analysis: | | |
|---|---|---|---|
| | Calcd. for $C_{14}H_8ClN_2O_3SNa.H_2O$ | Found for First Crop | Found for Second Crop |
| C | 46.48 | 46.99 | 46.71 |
| H | 3.06 | 2.68 | 2.70 |
| N | 7.74 | 7.98 | 7.79 |

The remainder of the first crop was redried. This afforded the anhydrous sodium salt of 5-chloro-3-(2-thenoyl)-2-oxindole-1-carboxamide, mp 237°–238° C.

| | Analysis: | |
|---|---|---|
| | Calcd. for $C_{14}H_8ClN_2O_3SNa$ | Found for Redried First Crop |
| C | 48.92 | 48.23 |
| H | 2.64 | 2.81 |
| N | 8.15 | 7.89 |

Part B

To a stirred slurry of 20 g. (62.4 mmole) of 5-chloro-3-(2-thenoyl)-2-oxindole-1-carboxamide in 400 ml. of methanol was added 4.14 ml. (68.6 mmole) of ethanolamine, dropwise, at room temperature. To the clear solution thus obtained, was added 6.74 g. of powdered sodium methoxide, and the mixture was stirred overnight. The solid which had formed was collected by filtration and dried under high vacuum overnight. This afforded the hemihydrate of 5-chloro-3-(2-thenoyl)-2-oxindole-1-carboxamide, mp. 238°–239° C.

| | Analysis: | |
|---|---|---|
| | Calcd. for $C_{14}H_8ClN_2O_3SNa.0.5H_2O$ | Found |
| C | 47.67 | 47.72 |
| H | 2.85 | 2.73 |
| N | 7.94 | 7.70 |

EXAMPLE 11

Potassium Salt of 5-Chloro-3-(2-thenoyl)-2-oxindole-1-carboxamide

The procedure of Example 10, Part B, was repeated, except that the powdered sodium methoxide was replaced by a solution of 7.00 g. of potassium hydroxide in methanol. This afforded the monohydrate of the potassium salt of 5-chloro-3-(2-thenoyl)-2-oxindole-1-carboxamide, mp 214°–216° C.

| | Analysis: | |
|---|---|---|
| | Calcd. for $C_{14}H_8ClN_2O_3SK.H_2O$ | Found |
| C | 44.30 | 44.29 |
| H | 2.93 | 2.67 |
| N | 7.41 | 7.22 |

EXAMPLE 12

Ammonium Salt of 5-Chloro-3-(2-thenoyl)-2-oxindole-1-carboxamide

The title salt was prepared substantially according to the procedure of Example 10, Part B, by using a solution of ammonia in methanol instead of powdered sodium methoxide. This afforded anhydrous title salt, mp 203°–204° C.

| | Analysis: | |
|---|---|---|
| | Calcd. for $C_{14}H_8ClN_2SO_3.NH_4$ | Found |
| C | 49.64 | 49.75 |
| H | 3.86 | 3.53 |
| N | 12.41 | 12.20 |

EXAMPLE 13

2-Oxindole-1-carboxamide

To a solution of 194 mg (1.0 mmole) of 2-(2-ureidophenyl)acetic acid in 4 ml of trifluoroacetic acid was added 630 mg (3.0 mmole) of trifluoroacetic anhydride, and the mixture was then heated under reflux for ca. 1 hour. The reaction mixture was cooled and the solvent was removed by evaporation in vacuo. The residue was triturated under 5–8 ml of saturated sodium bicarbonate solution, and the material which remained out of solution was collected by filtration. The solid thus obtained was recrystallized from ethanol to give 61 mg of the title compound as colorless needles, m.p. 179°–180° C. (slight decomposition).

Analysis: Calcd. for $C_9H_{18}N_2O_2$: C, 61.36; H, 4.58; N, 15.91%. Found: C, 61.40; H, 4.80; N, 15.77%.

EXAMPLE 14

5-Chloro-2-oxindole-1-carboxamide

Cyclization of 4.78 g (0.021 mole) of 2-(5-chloro-2-ureidophenyl)acetic acid with 8.0 g (0.063 mole) of trifluoroacetic anhydride in 75 ml of trifluoroacetic acid, according to the method of Example 13, followed by recrystallization of the crude product from acetonitrile, gave 80 mg of the title compound, m.p. 211° C. (dec.).

Analysis: Calcd. for $C_9H_7ClN_2O_2$: C, 51.32; H, 3.35; N, 13.30%. Found: C, 51.37; H, 3.37; N, 13.53%.

EXAMPLE 15

By cyclization of the 2-(2-ureidophenyl)acetic acid compounds from Preparation 3 with trifluoroacetic anhydride in trifluoroacetic acid, according to the procedure of Example 13, the following compounds can be prepared:
6-chloro-2-oxindole-1-carboxamide,
5-fluoro-2-oxindole-1-carboxamide,
6-fluoro-2-oxindole-1-carboxamide,
5-trifluoromethyl-2-oxindole-1-carboxamide and
6-trifluoromethyl-2-oxindole-1-carboxamide.

EXAMPLE 16

2-Oxindole-1-carboxamide

Chlorosulfonyl isocyanate (1.20 g, 8.4 mmole) was added to a mixture of 2-oxindole (0.94 g, 7.1 mmole) in ether (30 ml) and the reaction was stirred at room temperature for 20 hours. The ether was removed under vacuum and the residue was treated with water (10 ml) and 1N HCl (10 ml). Ethyl acetate (125 ml) was added and the mixture was stirred for one hour. The ethyl acetate phase was separated, washed with 1N HCl (1×50 ml), brine (2×100 ml) and dried (MgSO$_4$). Concentration afforded 0.97 g (77%) of crude product. Recrystallization from ethanol gave 0.18 g of the title product, m.p. 177°–179° C.

EXAMPLE 17

2-Oxindole-1-carboxamide

To a stirred mixture of 2-oxindole (5.86 g, 44.0 mmole) and dry toluene (160 ml) was added chlorosulfonyl isocyanate (7.47 g, 52.8 mmole). Hydrogen chloride was immediately evolved. The mixture was stirred under reflux for 15 minutes and then it was cooled to room temperature. Water (50 ml) was added to the cooled mixture (some HCl was initially evolved) and then the mixture was stirred for 1.5 hours. The solid which formed was collected by filtration and dried (4.10 g). The filtrate was extracted with ethyl acetate (100 ml), and the resulting extract was washed with brine (2×100 ml) and dried (MgSO$_4$). Evaporation of the extract under reduced pressure gave 4.16 g of solid. The combined solids were recrystallized by dissolution in acetonitrile (200 ml) followed by concentration of the solution under reduced pressure to about 75 ml. The small amount of amorphous material which separated was filtered off, the filtrate was decolorized and concentrated under reduced pressure to about 50 ml volume, then seeded. This gave the title compound as dark red crystals which were filtered off and dried (3.0 g; 38%).

EXAMPLE 18

6-Fluoro-5-methyl-2-oxindole-1-carboxamide

Following the procedure of Example 17, the title compound was prepared from 6-fluoro-5-methyl-2-oxindole (1.0 g, 6.0 mmole) and chlorosulfonyl isocyanate (1.03 g, 7.3 mmole) in toluene (30 ml). Water (5 ml) was used for the hydrolysis step. Yield=0.58 g, 46%, m.p. 200°–203° C.

Analysis: Calcd. for $C_{10}H_9N_2O_2F$: C, 57.69; H, 4.36; N, 13.46%. Found: C, 57.02; H, 4.41; N, 12.85%.

A sample of the chlorosulfonyl intermediate was removed prior to hydrolysis and subjected to mass spectral analysis for exact mass determination: $C_{10}H_8N_2O_4SCl$: 307.9848.

EXAMPLE 19

2-Oxindole-1-carboxamide

To a slurry of 2-oxindole (13.3 g, 0.10 mole) in toluene (150 ml) was added chlorosulfonyl isocyanate (15.6 g, 0.11 mole) and the reaction mixture was heated on a steam bath for ten minutes. (A clear solution formed within about three minutes, followed almost immediately by formation of a precipitate.) The reaction mixture was cooled in an ice bath for 30 minutes, and then the solid was filtered off and air dried.

The thus-obtained chlorosulfonyl intermediate was added to a 2:1 mixture of acetic acid/water (240 ml) and the resulting slurry was heated on a steam bath for ten minutes. It was cooled in an ice bath and the off-white solid which formed was filtered off and air dried. Concentration of the mother liquor to a slush and filtration thereof gave a further 1.2 g of product. The combined solids were recrystallized from about 250 ml of ethanol; yield=11.48 g (65%).

EXAMPLE 20

Substituted-2-oxindole-1-carboxamides

The following compounds were prepared by reaction of the appropriate 2-oxindole with chlorosulfonyl isocyanate, followed by hydrolysis, using the procedure of Example 19.

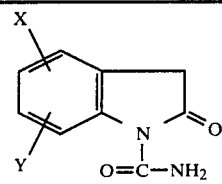

| | | Melting Point | Analysis Calculated | | | Analysis Found | | |
|---|---|---|---|---|---|---|---|---|
| X | Y | (°C.) | C | H | N | C | H | N |
| 5-CH$_3$ | H | 215–216d | | | | | | |
| 5-OCH$_3$ | H | 191–192 | | | | | | |
| 4-Cl | H | 201–202[1] | 51.32 | 3.35 | 13.30 | 51.04 | 3.26 | 13.24 |
| 5-Cl | H | 211d | 51.32 | 3.35 | 13.30 | 51.14 | 3.48 | 13.21 |
| 6-Cl | H | 221–222d | 51.32 | 3.35 | 13.30 | 51.07 | 3.30 | 13.31 |
| 5-F | H | 198[2] | 55.67 | 3.64 | 14.43 | 56.25 | 3.79 | 14.53 |
| 5-CF$_3$ | H | 214.5[2] | 49.19 | 2.89 | 11.48 | 48.90 | 3.05 | 11.50 |
| 4-CH$_3$ | 5-CH$_3$ | 222d | 64.69 | 5.92 | 13.72 | 64.57 | 5.94 | 13.64 |
| 5-CH$_3$ | 6-CH$_3$ | 214.5[3] | 64.69 | 5.92 | 13.72 | 64.52 | 6.67 | 13.68 |
| 5-Cl | 6-Cl | 245d | 44.11 | 2.47 | 11.43 | 43.98 | 2.55 | 11.58 |

[1]Recrystallized from ethanol
[2]Recrystallized from acetonitrile
[3]Recrystallized from acetic acid

EXAMPLE 21

5,6-Methylenedioxy-2-oxindole-1-carboxamide 5,6-Methylenedioxy-2-oxindole-1-carboxamide was prepared by reaction of 5,6-methylenedioxy-2-oxindole with chlorosulfonyl isocyanate, followed by hydrolysis, using the procedure of Example 19. The product melted at 237°–238° C. (dec.) after recrystallization from acetic acid.

EXAMPLE 22

By reaction of the appropriate 2-oxindole with chlorosulfonyl isocyanate, followed by hydrolysis, using the procedure of Example 19, the following compounds can be prepared.

| X | Y |
|---|---|
| 5-n-OC$_4$H$_9$ | H |
| 5-OC$_2$H$_5$ | H |
| 7-Cl | H |
| 5-n-C$_4$H$_9$ | H |
| 5-n-SC$_4$H$_9$ | H |
| 6-OCH$_3$ | H |
| 6-n-SC$_4$H$_9$ | H |
| 5-CH(CH$_3$)$_2$ | H |
| 6-n-C$_4$H$_9$SO | H |
| 6-n-C$_4$H$_9$SO$_2$ | H |
| H | 5-Br |
| 6-n-C$_3$H$_7$CO | H |
| 5-(CH$_3$)$_2$CHCONH | H |
| 5-SO$_2$N(CH$_3$)$_2$ | H |
| 5-SO$_2$N(n-C$_3$H$_7$)$_2$ | H |

EXAMPLE 23

By reaction of the appropriate 2-oxindole with chlorosulfonyl isocyanate, followed by hydrolysis, using the procedure of Example 19, the following tricyclic compounds can be prepared:

| X and Y* |
|---|
| 4-CH$_2$—CH$_2$—CH$_2$—5 |
| 5-CH$_2$—CH$_2$—CH$_2$—6 |
| 6-CH$_2$—CH$_2$—CH$_2$—CH$_2$—7 |
| 5-CH=CH—CH=CH—6 |
| 5-O—CH$_2$—CH$_2$—6 |
| 5-CH$_2$—CH$_2$—O—6 |
| 5-S—CH$_2$—CH$_2$—6 |
| 5-O—CH=CH—6 |
| 5-S—CH=CH—6 |
| 5-CH=CH—S—6 |

*In this column, the numeral to the left of the formula indicates the point attachment of that end of the formula to the 2-oxindole nucleus and the numeral to the right indicates the point of attachment of that end of the formula to the 2-oxindole nucleus.

EXAMPLE 24

6-Methylthio-2-oxindole-1-carboxamide

Chlorosulfonyl isocyanate (5.66 g, 0.04 mole) was added to a slurry of 6-methylthio-2-oxindole (6.0 g, 0.033 mole) in acetonitrile (60 ml) at 5° to 10° C. The reaction mixture was stirred for one hour. Water (100 ml) was then added and stirring was continued for ten minutes. The aqueous solution was extracted with ethyl acetate (600 ml), which was then washed successively with water and brine, dried (MgSO$_4$) and evaporated under reduced pressure to give a gray solid which was recrystallized from acetonitrile. Yield=3.0 g. An additional 0.71 g of product was obtained from the mother liquor. Total yield=3.71 g (50.6%); m.p. 176°–179° C.

EXAMPLE 25

5,6-Dimethoxy-2-oxindole-1-carboxamide

Following the procedure of Example 24, the title compound was prepared from 5,6-dimethoxy-2-oxindole (8.0 g, 0.042 mole), chlorosulfonyl isocyanate (7.08 g, 0.05 mole) and acetonitrile (75 ml). The crude product obtained upon evaporation of the ethyl acetate extract was recrystallized from acetonitrile/acetic acid (1:1). Yield=6.02 g (60%); m.p. 206.5°–209° C.

EXAMPLE 26

6-Trifluoromethyl-2-oxindole-1-carboxamide

To a slurry of 6-trifluoromethyl-2-oxindole (8.0 g, 0.04 mole) in acetonitrile (80 ml) was added chlorosulfonyl isocyanate (6.65 g, 0.047 mole) and the mixture was stirred for 45 minutes. Water (100 ml) was then added and the aqueous mixture was stirred for one hour. The precipitate which formed was filtered off and recrystallized from acetonitrile to give 0.92 g of the title product. Extraction of the filtrate from the aqueous reaction mixture with ethyl acetate (300 ml) followed by drying the extract over MgSO$_4$ and then evaporating it under reduced pressure gave additional product. Recrystallization from acetonitrile gave an additional 2.2 g of product.

Additional product (1.85 g) was recovered by combining the mother liquors from the acetontrile recrystallizations and concentrating them under reduced pressure. Total yield=4.97 g (51%); m.p. 207.5°–210° C.

EXAMPLE 27

Repetition of the procedure of Example 26 but using the appropriate substituted 2-oxindole afforded the following compounds.

| X | Y | Melting Point (°C.) |
|---|---|---|
| 4-SCH$_3$ | H | 181–184 |
| 6-F | H | 191.5–194 |
| 6-Br | H | 205–208 |
| 5-NO$_2$ | H | 201–205 |
| 5-F | 6-Cl | 229–231[1] |
| 5-F | 6-F | 198–201 |

[1] Reaction run in toluene as solvent. Both the starting material and the product were contaminated with some of the corresponding 4-chloro-5-fluoro-isomer.

EXAMPLE 28

6-Phenyl-2-oxindole-1-carboxamide

To 4.5 g. (21.5 mmole) of 6-phenyl-2-oxindole in a mixture of 100 ml. of toluene and 25 ml. of tetrahyrofuran was added, with stirring, at 5° C., 2.2 ml. (25.8 mmole) of chlorosulfonyl isocyanate. Stirring was continued for 1 hour at 0°–5° C. and then 100 ml. of water was added. The solid was recovered by filtration and added to a mixture of 40 ml. of glacial acetic acid and 80 ml. of water. The resulting mixture was heated at 100° C. for 1 hour, cooled and filtered. The residue was dried to give 3.1 g. of the title compound, mp. 188°–189° C.

EXAMPLE 29

5-Benzoyl-2-oxindole-1-carboxamide

A mixture of 10.1 g. (42 mmole) of 5-benzoyl-2-oxindole, 4.4 ml. (51 mmole) of chlorosulfonyl isocyanate and 300 ml. of tetrahydrofuran was stirred at room temperature for 6 hours, and then the solvent was removed by evaporation in vacuo. The residue was added to 150 ml. of glacial acetic acid and 300 ml. of water and the resulting mixture was heated under reflux for 2 hours. The reaction mixture was cooled and the supernatant liquid was removed by decantation. The remaining gummy residue was triturated under acetonitrile to give a solid which was recovered by filtration and then recrystallized from a 1:1 mixture of n-propanol and acetonitrile. This gave 4.1 g. of the title compound as a solid, mp. 210°–211° C.

EXAMPLE 30

Reaction of 5-acetyl-2-oxindole and 5-(2-thenoyl)-2-oxindole with chlorosulfonyl isocyanate, followed by hydrolysis with aqueous acetic acid, substantially according to the procedure of Example 29, afforded the following compounds:
5-acetyl-2-oxindole-1-carboxamide, 34% yield, mp 225° C. (dec.) (from CH$_3$CN) and
5-(2-thenoyl)-2-oxindole-1-carboxamide, 51% yield, mp 200° C. (dec.) (from CH$_3$OH/CH$_3$CN), respectively.

EXAMPLE 31

5-Acetamido-2-oxindole-1-carboxamide

A slurry of 0.5 g. (2.6 mmole) of 5-amino-2-oxindole-1-carboxamide and 0.35 g. of 4-(N,N-dimethylamino)-pyridine was stirred at 10° C., and then 0.20 ml. (2.8 mmole) of acetyl chloride was added. Stirring was continued at ca −10° C. for 20 minutes and at room temperature for 15 minutes, and then 20 ml. of 1N hydrochloric acid was added. The solid was recovered by filtration, and dried, to give 0.20 g. of the title compound as a cream-colored solid.

By substituting butanoyl chloride for acetyl chloride in the above procedure, 5-butanamido-2-oxindole-1-carboxamide can be prepared.

EXAMPLE 32

5-Benzamido-2-oxindole-1-carboxamide

Acylation of 5-amino-2-oxindole-1-carboxamide with benzoyl chloride substantially according to the procedure of Example 31 afforded a 90% yield of the title compound as a cream-colored solid, mp 223°–226° C.

EXAMPLE 33

4-Methylsulfonyl-2-oxindole-1-carboxamide

The title compound was prepared by oxidation of 2.5 g. of 4-methylthio-2-oxindole-1-carboxamide with 2.4 molar equivalents of 3-chloroperbenzoic acid in tetrahydrofuran at room temperature, according to standard procedures. The product was isolated as a solid (0.81 g., 28% yield).

EXAMPLE 34

6-Methylsulfonyl-2-oxindole-1-carboxamide

Oxidation of 1.25 g. of 6-methylthio-2-oxindole-1-carboxamide with 2.1 molar equivalents of 3-chloroperbenzoic acid in tetrahydrofuran at room temperature, according to standard procedures, afforded 1.13 g. of the title compound, contaminated with the corresponding sulfoxide.

EXAMPLE 35

4-Methylsulfinyl-2-oxindole-1-carboxamide

Oxidation of 1.0 g. of 4-methylthio-2-oxindole-1-carboxamide with 1.1 molar equivalents of 3-chloroperbenzoic acid in tetrahydrofuran at ca 0° C. afforded 0.9 g. of the title compound, mp 198.5°–200° C.

In analogous fasion, oxidation of 6-methylthio-2-oxindole-1-carboxamide with 3-chloroperbenzoic acid gave 6-methylsulfinyl-2-oxindole-1-carboxamide.

EXAMPLE 36

3-(2-Furoyl)-6-fluoro-2-oxindole-1-carboxamide

Following substantially the procedure of Example 24, the title compound was prepared in 17% yield from 3-(2-furoyl)-6-fluoro-2-oxindole (0.30 g, 1.2 mmole), chlorosulfonyl isocyanate (0.20 g, 1.4 mmole), acetonitrile (15 ml) and water (10 ml). Yield=60 mg, m.p. 231°–235° C.

EXAMPLE 37

3-(2-Thenoyl)-5-chloro-2-oxindole-1-carboxamide

To a stirred slurry of 1.5 g. (5.4 mmole) of 3-(2-thenoyl)-5-chloro-2-oxindole in 15 ml. of dry acetonitrile was added 0.52 ml. (5.9 mmole) of chlorosulfonyl isocyanate, and the reaction mixture was stirred at room temperature for 2 hours. A small sample was removed, filtered and evaporated in vacuo to give a small sample of N-chlorosulfonyl-3-(2-thenoyl)-5-chloro-2-oxindole-1-carboxamide, mp 166°–169° C. To the remainder of the reaction mixture, 30 ml. of water was added slowly with stirring and stirring was continued for 1 hour. The reaction mixture was then poured into 50 ml. of 1N hydrochloric acid containing ice chips, and the resulting mixture was stirred for 20 minutes. The yellow solid was recovered by filtration, washed with water and diisopropyl ether and recrystallized from glacial acetic acid to give 200 mg. of a first crop of the title compound, mp 213°–215° C. The mother liquors from which the first crop had been recovered deposited a further yellow solid. The latter solid was recovered by filtration to give 470 mg. of a second crop of the title compound. The second crop was recrystallized from glacial acetic acid and combined with the first crop and recrystallized from glacial acetic acid. This gave 280 mg. of the title compound, mp 232°–234° C.

PREPARATION 1

2-(2-Ureidophenyl)acetic Acid

A slurry of 2.9 g (0.01 mole) of N-cyclohexylcarbonyl-2-oxindole-1-carboxamide in 50 ml of 1N potassium hydroxide solution was stirred at room temperature for ca. 30 minutes, during which time the solid went into solution. At this point, the reaction mixture was acidified with concentrated hydrochloric acid, with ice cooling, and then it was extracted with ethyl acetate. The extracts were washed with saturated sodium chloride solution, dried (Na$_2$SO$_4$) and evaporated in vacuo to give an oily solid. The oily solid was washed with diisopropyl ether and then it was recrystallized from ethanol to give 70 mg of the title compound, m.p. 174.5° C. (dec.).

Analysis: Calcd. for C$_9$H$_{10}$N$_2$O$_3$: C, 55.66; H, 5.19; N, 14.43%. Found: C, 55.37; H, 5.33; N, 14.38%.

PREPARATION 2

2-(5-Chloro-2-ureidophenyl)acetic Acid

The title compound was prepared in 43% yield by hydrolysis of N-isobutyryl-5-chloro-2-oxindole-1-carboxamide with 1N potassium hydroxide, substantially according to the procedure of Preparation 1. After hydrolysis was complete and the reaction mixture was acidified, the product precipitated. It was recovered by filtration and recrystallized from ethanol to give the title compound as colorless crystals, m.p. 187.5° C. (dec.).

Analysis: Calcd. for C$_9$H$_9$ClN$_2$O$_3$: C, 47.28; H, 3.97; N, 12.26%. Found: C, 47.11; H, 3.98; N, 12.20%.

PREPARATION 3

By hydrolysis of the N-isobutyryl-2-oxindole-1-carboxamides of Preparation 6 with potassium hydroxide, using the procedure of Preparation 1, the following compounds can be prepared:
2-(4-chloro-2-ureidophenyl)acetic acid,
2-(5-fluoro-2-ureidophenyl)acetic acid,
2-(4-fluoro-2-ureidophenyl)acetic acid,
2-(5-trifluoromethyl-2-ureidophenyl)acetic acid and
2-(4-trifluoromethyl-2-ureidophenyl)acetic acid.

PREPARATION 4

N-Cyclohexylcarbonyl-2-oxindole-1-carboxamide

To a stirred slurry of 20.0 g (0.15 mole) of 2-oxindole in 150 ml of toluene was added 29.6 g (0.19 mole) of cyclohexylcarbonyl isocyanate. The mixture was heated under reflux for ca. 30 minutes and then it was cooled to room temperature. The solid was recovered by filtration and then it was recrystallized from ethanol. This afforded 26.5 g of the title compound as fluffy, colorless crystals, m.p. 144.5°–145.5° C.

Analysis: Calcd. for C$_{16}$H$_{18}$N$_2$O$_3$: C, 67.11; H, 6.34; N, 9.79%. Found: C, 67.00; H, 6.36; N, 9.77%.

PREPARATION 5

N-Isobutyryl-5-chloro-2-oxindole-1-carboxamide

To a stirred slurry of 8.38 g (0.05 mole) of 5-chloro-2-oxindole in 250 ml of toluene was added 6.79 g (0.06 mole) of isobutyryl isocyanate, and the reaction mixture was heated under reflux for 5.5 hours. The reaction mixture was cooled to room temperature, a small amount of insoluble material was removed by filtration, and then the solvent was removed by evaporation in vacuo. The residue was recrystallized from acetonitrile (with the aid of decolorizing carbon), followed by recrystallization from ethanol, to give 3.23 g of the title compound as pink crystals, m.p. 139°–141° C.

Analysis: Calcd. for C$_{13}$H$_{13}$ClN$_2$O$_3$: C, 55.62; H, 4.67; N, 9.98%. Found: C, 55.53; H, 4.48; N, 9.97%.

PREPARATION 6

By reaction of the appropriately substituted 2-oxindole with isobutyryl isocyanate, using the procedure of Preparation 5, the following compounds can be prepared:
N-isobutyryl-6-chloro-2-oxindole-1-carboxamide,
N-isobutyryl-5-fluoro-2-oxindole-1-carboxamide,
N-isobutyryl-6-fluoro-2-oxindole-1-carboxamide,
N-isobutyryl-5-trifluoromethyl-2-oxindole-1-carboxamide and
N-isobutyryl-6-trifluoromethyl-2-oxindole-1-carboxamide.

PREPARATION 7

5-Chloro-2-oxindole

To a stirred slurry of 100 g (0.55 mol) of 5-chloroisatin in 930 ml of ethanol was added 40 ml (0.826 mol) of hydrazine hydrate, resulting in a red solution. The solution was heated under reflux for 3.5 hours, during which time a precipitate appeared. The reaction mixture was stirred overnight, and then the precipitate was recovered by filtration to give 5-chloro-3-hydrazono-2-oxindole as a yellow solid, which was dried in a vacuum oven. The dried solid weighed 105.4 g.

The dried solid was then added portionwise, during 10 minutes, to a solution of 125.1 g of sodium methoxide in 900 ml of absolute ethanol. The resultant solution was heated under reflux for 10 minutes and then it was concentrated in vacuo to a gummy solid. The gummy solid was dissolved in 400 ml of water and the aqueous solution thus obtained was decolorized with activated carbon and then poured into a mixture of 1 liter of water and 180 ml of concentrated hydrochloric acid containing ice chips. A tan solid precipitated and it was collected by filtration and washed thoroughly with water. The solid was dried and then it was washed with diethyl ether. Finally it was recrystallized from ethanol to give 48.9 g of the title compound, m.p. 193°–195° C. (dec).

In an analogous fashion, 5-methylisatin was converted into 5-methyl-2-oxindole by treatment with hydrazine hydrate followed sodium ethoxide in ethanol. The product melted at 173°–174° C.

PREPARATION 8

4,5-Dimethyl-2-oxindole and 5,6-dimethyl-2-oxindole 3,4-Dimethylaniline was converted into 3,4-dimethylisonitrosoacetanilide by reaction with chloral hydrate and hydroxylamine, using the method described in "Organic Syntheses," Collective Volume I, page 327. The 3,4-dimethyl-isonitrosoacetanilide was cyclized with sulfuric acid, according to the method of Baker et al., *Journal of Organic Chemistry*, 17, 149 (1952), to give 4,5-dimethylisatin (m.p. 225°–226° C.) and 5,6-dimethylisatin (m.p. 217°–218° C.).

4,5-Dimethylisatin was converted into 4,5-dimethyl-2-oxindole, m.p. 245.5°–247.5° C., by treatment with hydrazine hydrate, followed by sodium ethoxide in ethanol, substantially according to the procedure of Preparation 7.

In like manner, 5,6-dimethylisatin was converted into 5,6-dimethyl-2-oxindole, m.p. 196.5°–198° C., by treatment with hydrazine hydrate, followed by sodium ethoxide in ethanol, substantially according to the procedure of Preparation 7.

PREPARATION 9

4-Chloro-2-oxindole and 6-chloro-2-oxindole

A. 3-Chloro-isonitrosoacetanilide

To a stirred solution of 113.23 g (0.686 mol) of chloral hydrate in 2 liters of water was added 419 g (2.95 mol) of sodium sulfate, followed by a solution prepared from 89.25 g (0.70 mol) of 3-chloroaniline, 62 ml of concentrated hydrochloric acid and 500 ml of water. A thick precipitate formed. To the reaction mixture was then added, with stirring, a solution of 155 g (2.23 mol) of hydroxylamine in 500 ml of water. Stirring was continued and the reaction mixture was warmed slowly and it was maintained between 60° and 75° C. for approximately 6 hours, during which time an additional 1 liter of water had been added to facilitate stirring. The reaction mixture was then cooled and the precipitate was recovered by filtration. The wet solid was dried to give 136.1 g of 3-chloro-isonitrosoacetanilide.

B. 4-Chloroisatin and 6-chloroisatin

To 775 ml of concentrated sulfuric acid, preheated to 70° C., was added, with stirring, 136 g of 3-chloroisonitrosoacetanilide at such a rate as to maintain the reaction medium at a temperature between 75° and 85° C. When all the solid had been added, the reaction mixture was heated at 90° C. for an additional 30 minutes. The reaction mixture was then cooled, and poured slowly onto ca. 2 liters of ice, with stirring. Additional ice was added as necessary to maintain the temperature below room temperature. A red-orange precipitate formed which was recovered by filtration, washed with water and dried. The resultant solid was slurried in 2 liters of water, and then it was brought into solution by the addition of ca. 700 ml of 3N sodium hydroxide. The solution was filtered, and then pH was adjusted to 8 with concentrated hydrochloric acid. At this point, 120 ml of a mixture of 80 parts water and 20 parts concentrated hydrochloric acid was added. The solid which precipitated was recovered by filtration, washed with water and dried to give 50 g of crude 4-chloroisatin. The filtrate from which the 4-chloroisatin had been recovered was further acidified to pH 0 using concentrated hydrochloric acid, whereupon a further precipitate formed. It was recovered by filtration, washed with water and dried, to give 43 g of crude 6-chloroisatin.

The crude 4-chloroisatin was recrystallized from acetic acid to give 43.3 g of material melting at 258°–259° C.

The crude 6-chloroisatin was recrystallized from acetic acid to give 36.2 g of material melting at 261°–262° C.

C. 4-Chloro-2-oxindole

To a stirred slurry of 43.3 g of 4-chloroisatin in 350 ml of ethanol was added 17.3 ml of hydrazine hydrate, and then the reaction mixture was heated under reflux for 2 hours. The reaction mixture was cooled, and the precipitate was recovered by filtration to give 43.5 g of 4-chloro-3-hydrazono-2-oxindole, m.p. 235°–236° C.

To a stirred solution of 22 g of sodium in 450 ml of anhydrous ethanol was added, portionwise, 43.5 g of 4-chloro-3-hydrazono-2-oxindole, and the resulting solution was heated under reflux for 30 minutes.

The cooled solution was then concentrated to a gum, which was dissolved in 400 ml of water and decolorized using activated carbon. The resulting solution was poured onto a mixture of 1 liter of water and 45 ml of concentrated hydrochloric acid. The precipitate which formed was recovered by filtration, dried and recrystallized from ethanol, giving 22.4 g of 4-chloro-2-oxindole, m.p. 216°–218° C. (dec).

D. 6-Chloro-2-oxindole

Reaction of 36.2 g of 6-chloroisatin with hydrazine hydrate followed by sodium ethoxide in ethanol, substantially according to C above, afforded 14.2 g of 6-chloro-2-oxindole, m.p. 196°–198° C.

PREPARATION 10

5,6-Difluoro-2-oxindole

Reaction of 3,4-difluoroaniline with chloral hydrate and hydroxylamine followed cyclization with sulfuric acid, in a manner analogous to Parts A and B of Preparation 9, gave 5,6-difluoroisatin, which was reacted with hydrazine hydrate followed by sodium methoxide in ethanol, in a manner analogous to Preparation 7, to give the title compound, m.p. 187°–190° C.

PREPARATION 11

5-Fluoro-2-oxindole

To a stirred solution of 11.1 g (0.1 mol) of 4-fluoroaniline in 200 ml of dichloromethane, at −60° to −65° C., was added, dropwise, a solution of 10.8 g (0.1 mol) of t-butyl hypochlorite in 25 ml of dichloromethane. Stirring was continued for 10 minutes at −60° to −65° C., and then was added, dropwise, a solution of 13.4 g (0.1 mol) of ethyl 2-(methylthio)acetate in 25 ml of dichloromethane. Stirring was continued at −60° C. for 1 hour and then was added, dropwise, at −60° to −65° C., a solution of 11.1 g (0.11 mol) of triethylamine in 25 ml of dichloromethane. The cooling bath was removed, and when the reaction mixture had warmed to room temperature, 100 ml of water was added. The phases were separated, and the organic phase was washed with saturated sodium chloride solution, dried ($Na_2SO_4$) and evaporated in vacuo. The residue was dissolved in 350 ml of diethyl ether, to which was added 40 ml of 2N hydrochloric acid. This mixture was stirred at room temperature overnight. The phases were separated and the ether phase was washed with water, followed saturated sodium chloride. The dried ($Na_2SO_4$) ether phase was evaporated in vacuo to give 17 g of an orange-brown solid which was triturated under isopropyl ether. The solid was then recrystallized form ethanol, to give 5.58 g of 5-fluoro-3-methylthio-2-oxindole, m.p. 151.5°–152.5° C.

Analysis: Calcd. for $C_9H_8ONFS$: C, 54.80; H, 4.09; N, 7.10%. Found: C, 54.74; H, 4.11; N, 7.11%.

A sample of the above 5-fluoro-3-methylthio-2-oxindole (986 mg, 5.0 mmol) was added to 2 teaspoonsful of Raney nickel under 50 ml of absolute ethanol, and then the reaction mixture was heated under reflux for 2 hours. The catalyst was removed by decantation and was washed with absolute ethanol. The combined ethanol solutions were evaporated in vacuo and the residue was dissolved in dichloromethane. The dichloromethane solution was dried ($Na_2SO_4$) and evaporated in vacuo to give 475 mg of 5-fluoro-2-oxindole, m.p. 121°–134° C.

In analogous fashion, 4-trifluoromethylaniline was reacted with t-butyl hypochlorite, ethyl 2-(methylthio)acetate and triethylamine followed by reduction of the 3-thiomethyl-5-trifluoromethyl-2-oxindole thus obtained with Raney nickel, to give 5-trifluoromethyl-2-oxindole, m.p. 189.5°–190.5° C.

PREPARATION 12

5-Methoxy-2-oxindole

5-Methoxy-2-oxindole was prepared from 4-methoxyaniline in a manner similar to the procedure of Preparation 11, except that the initial chlorination step was carried out using a solution of chlorine gas in dichloromethane in place of t-butyl hypochlorite. The title product melted at 150.5°–151.5° C.

PREPARATION 13

6-Chloro-5-fluoro-2-oxindole

To 130 ml of toluene was added, with stirring, 24.0 g (0.165 mole) of 3-chloro-4-fluoroaniline and 13.5 ml (0.166 mole) of pyridine. The resulting solution was cooled to ca. 0° C. and 13.2 ml (0.166 mole) of 2-chloroacetyl chloride was added. The reaction mixture was stirred at room temperature for 5 hours and then it was extracted twice with 100 ml of 1N hydrochloric acid, followed by 100 ml of saturated sodium chloride solution. The resulting toluene solution was dried using magnesium sulfate, and then it was concentrated in vacuo to give 32.6 g (88% yield) of N-(2-chloroacetyl)-3-chloro-4-fluoroaniline.

A 26.63-g sample of the N-(2-chloroacetyl)-3-chloro-4-fluoroaniline was thoroughly mixed with 64 g of anhydrous aluminum chloride, and the mixture was heated at 210°–230° C. for 8.5 hours. The reaction mixture was then poured onto a mixture of ice and 1N hydrochloric acid, with stirring. Stirring was continued for 30 minutes, and then the solid was collected by filtration (22.0 g). The solid was dissolved in 1:1 ethyl acetate-hexane and chromatographed on 800 g of silica gel. Elution of the column, followed by evaporation of the fractions, produced 11.7 g of the N-(2-chloroacetyl)-3-chloro-4-fluoroaniline, followed by 3.0 g of 6-chloro-5-fluoro-2-oxindole. The latter material was recrystallized from toluene to give 1.70 g (7% yield) of the title compound, m.p. 196°–206° C. Analysis by NMR spectroscopy indicated that the product was contaminated by some 4-chloro-5-fluoro-2-oxindole.

PREPARATION 14

6-Fluoro-5-methyl-2-oxindole

An intimate mixture of 11.62 g (57.6 mmol) of N-(2-chloroacetyl)-3-fluoro-4-methylaniline and 30.6 g (229.5 mmol) of anhydrous aluminum chloride was heated to 210°–220° C. After 4 hours, the reaction mixture was cooled and then added to 100 ml of 1N hydrochloric acid and 50 ml of ice. A tan solid formed, which was collected by filtration and recrystallized from aqueous ethanol. Three crops were obtained, weighing 4.49 g, 2.28 g and 1.0 g, respectively. The crop weighing 1.0 g was further recrystallized from water to give 280 mg of the title compound, m.p. 168.5°–171° C.

PREPARATION 15

6-Bromo-2-oxindole

To 9.4 g of sodium hydride was added 195 ml of dimethyl sulfoxide, followed by the dropwise addition of 22.37 ml of dimethyl malonate. At the end of the addition, the mixture was heated to 100° C. and maintained at that temperature for 40 minutes. At this point, 25 g of 1,4-dibromo-2-nitrobenzene was added all at once. The reaction mixture was maintained at 100° C. for 4 hours and then it was added to 1.0 liter of saturated ammonium chloride solution. The resulting mixture was extracted with ethyl acetate and the extracts were washed with ammonium chloride solution, water and saturated sodium chloride. The dried (MgSO4) solvent was evaporated, and the residue was recrystallized from ethyl acetate-hexane to give 22.45 g of dimethyl 2-(4-bromo-2-nitrophenyl)malonate.

A solution of 17.4 g of dimethyl 2-(4-bromo-2-nitrophenyl)malonate and 4.6 g of lithium chloride in 150 ml of dimethyl sulfoxide was placed in an oil bath at 100° C. After 3 hours, the reaction mixture was cooled to room temperature and then it was poured into a mixture of 500 ml of ethyl acetate and 500 ml of saturated sodium chloride solution. The layers were separated and the aqueous layer was extracted with further ethyl acetate. The combined organic layers were washed with saturated sodium chloride solution, dried using sodium sulfate, and then evaporated in vacuo. The residue was chromatographed using silica gel as adsorbant and ethyl acetate-hexane mixture as eluant. This afforded 9.4 g of methyl 2-(4-bromo-2-nitrophenyl)-acetate.

To a solution of 7.4 g of methyl 2-(4-bromo-2-nitrophenyl)acetate in 75 ml of acetic acid was added 6.1 g of iron powder. The reaction mixture was placed in an oil bath at 100° C. After 1 hour, the solvent was removed by evaporation in vacuo, and the residue was dissolved in 250 ml of ethyl acetate. The solution was filtered, washed with saturated sodium chloride solution, dried using sodium sulfate, decolorized using activated carbon, and evaporated in vacuo. This afforded 5.3 g of 6-bromo-2-oxindole as a white crystalline solid, m.p. 213°–214° C.

In like manner, starting with 1,4,5-trichloro-2-nitrobenzene, 5,6-dichloro-2-oxindole was prepared, m.p. 209°–210° C.

PREPARATION 16

6-Phenyl-2-oxindole

To 3.46 g. (0.072 mole) of sodium hydride was added 50 ml. of dimethyl sulfoxide followed by the dropwise addition of a solution of 8.2 ml. (0.072 mole) of dimethyl malonate in 10 ml. of dimethyl sulfoxide, with stirring. After completion of the addition, stirring was continued for 1 hour, and then a solution of 10 g. (0.036 mole) of 4-bromo-3-nitrodiphenyl in 50 ml. of dimethyl sulfoxide was added. The reaction mixture was heated to 100° C. for 1 hour, cooled, and poured onto a mixture of ice-water containing 5 g. of ammonium chloride. The mixture thus obtained was extracted with ethyl acetate, and the extracts were washed with sodium chloride solution and dried using magnesium sulfate. Evaporation in vacuo to give an oil, which was chromatographed using silica gel and then recrystallized from methanol to afford 6 g. of dimethyl 2-(3-nitro-4-diphenylyl)-malonate, m.p. 82°–83° C.

A portion (5 g.) of the above nitro compound was reduced with hydrogen over a platinum catalyst, in a mixture of 50 ml. of tetrahydrofuran and 10 ml. of methanol, at a pressure of ca 5 kg/cm$^2$, to give the corresponding amine. The latter compound was refluxed in ethanol for 16 hours, and then the product was recovered by solvent evaporation and recrystallized from methanol to give 1.1 g. of ethyl 6-phenyl-2-oxindole-1-carboxylate, m.p. 115°–117° C.

The above ethyl ester (1.0 g.) and 100 ml. of 6N hydrochloric acid was heated under reflux for 3 hours and then allowed to stand at room temperature for 3 days. The solid was collected by filtration and dried, to give 700 mg. of 6-phenyl-2-oxindole, m.p. 175°–176° C.

PREPARATION 17

5-Acetyl-2-oxindole

To 95 ml. of carbon disulfide was added 27 g. (0.202 mole) of aluminum chloride, followed by the dropwise addition of a solution of 3 ml. (0.042 mole) of acetyl chloride in 5 ml. of carbon disulfide, with stirring. Stirring was continued for 5 minutes and then 4.4 g. (0.033 mole) of 2-oxindole was added. The resulting mixture was heated under reflux for 4 hours and cooled. The carbon disulfide was removed by decantation and the residue was triturated under water and recovered by filtration. After drying, 3.2 g. of the title compound was obtained, m.p. 225°–227° C.

Reaction of 2-oxindole with benzoyl chloride and with 2-thenoyl chloride in the presence of aluminum chloride, substantially according to the above procedure, afforded the following compounds:
5-benzoyl-2-oxindole, m.p. 203°–205° C. (from $CH_3OH$) and
5-(2-thenoyl)-2-oxindole, m.p. 211°–213° C. (from $CH_3CN$).

PREPARATION 18

5-Bromo-2-oxindole can be prepared by bromination of 2-oxindole; see further Beckett et al., *Tetrahedron*, 24, 6093 (1968) and Sumpter et al., *Journal of the American Chemical Society*, 67, 1656 (1945).

5-n-Butyl-2-oxindole can be prepared by reaction of 5-n-butylisatin with hydrazine hydrate followed by sodium methoxide in ethanol, according to the procedure of Preparation 7. 5-n-Butylisatin can be prepared from 4-n-butylaniline by treatment with chloral hydrate and hydroxylamine, followed by cyclization with sulfuric acid, according to the procedure of Parts A and B of Preparation 9.

5-Ethoxy-2-oxindole can be prepared by conversion of 3-hydroxy-6-nitro-toluene into 3-ethoxy-6-nitrotoluene by standard methods (potassium carbonate and ethyl iodide in acetone), followed by conversion of the 3-ethoxy-6-nitrotoluene into 5-ethoxy-2-oxindole by the method described by Beckett et al., *Tetrahedron*, 24, 6093 (1968), for the conversion of 3-methoxy-6-nitrotoluene into 5-methoxy-2-oxindole. 5-n-Butoxy-2-oxindole can be prepared in like manner, but substituting n-butyl iodide for ethyl iodide.

5,6-Dimethoxy-2-oxindole can be prepared by the method of Walker, *Journal of the American Chemical Society*, 77, 3844 (1955).

7-Chloro-2-oxindole can be prepared by the method described in U.S. Pat. No. 3,882,236.

4-Thiomethyl-2-oxindole and 6-thiomethyl-2-oxindole can be prepared by the method described in U.S. Pat. No. 4,006,161. 5-n-Butylthio-2-oxindole can be prepared in like manner, but substituting 4-butylthioaniline for the 3-methylthioaniline.

5,6-Methylenedioxy-2-oxindole can be prepared by the method of McEvoy et al., *Journal of Organic Chemistry*, 38, 3350 (1973). 5,6-Ethylenedioxy-2-oxindole can be prepared in analogous fashion.

6-Fluoro-2-oxindole can be prepared according to Protiva et al., *Collection of Czechoslovakian Chemical Communications*, 44, 2108 (1979) and U.S. Pat. No. 4,160,032.

6-Trifluoromethyl-2-oxindole can be prepared according to Simet, *Journal of Organic Chemistry*, 28, 3580 (1963).

6-Methoxy-2-oxindole can be prepared according to Wieland et al., *Chemische Berichte*, 96, 253 (1963).

5-Nitro-2-oxindole can be prepared by the method of Sumpter et al., *Journal of the American Chemical Society*, 67, 499 (1945).

5-Cyclopropyl-2-oxindole and 5-cycloheptyl-2-oxindole can be prepared by reaction of 5-cyclopropylisatin and 5-cycloheptylisatin, repsectively, with hydrazine hydrate followed by sodium methoxide in ethanol, according to the procedure of Preparation 7. 5-Cyclopropylisatin and 5-cycloheptylisatin can be prepared from 4-cyclopropylaniline and 4-cycloheptylaniline, respectively, by treatment with chloral hydrate and hydroxylamine, followed by cyclization with sulfuric acid, according to Parts A and B of Preparation 9.

PREPARATION 19

3-(2-Furoyl)-2-oxindole

To a stirred solution of 5.5 g (0.24 mole) of sodium in 150 ml of ethanol was added 13.3 g (0.10 mole) of 2-oxindole at room temperature. The resulting slurry was cooled to ice-bath temperature, and then 15.7 g (0.12 mole) of 2-furoyl chloride was added, dropwise, during 10–15 minutes. The ice-bath was removed, and an additional 100 ml of ethanol was added and then the reaction mixture was heated under reflux for 7 hours. The reaction mixture was allowed to stand overnight and then the solid was filtered off. The solid was added to 400 ml of water and the resulting mixture was acidified using concentrated hydrochloric acid. The mixture was cooled with ice and the solid was collected by filtration. The solid residue was recrystallized from 150 ml of acetic acid, affording 8.3 g of yellow crystals, m.p. 209°–210° C. (dec.).

Analysis: Calcd. for $C_{13}H_9O_3N$: C, 68.72; H, 3.99; N, 6.17%. Found: C, 68.25; H, 4.05; N, 6.20%.

PREPARATION 20

Reaction of 2-oxindole with the appropriate acid chloride using the method of Preparation 19, gave the following additional products:
3-(2-thenoyl)-2-oxindole, m.p. 189°–190° C., 17% yield;
3-(2-[2-thienyl]acetyl)-2-oxindole, m.p. 191°–192.5° C., 38% yield; and
3-(2-phenoxyacetyl)-2-oxindole, m.p. 135°–136° C., 42% yield.

PREPARATION 21

3-(3-Furoyl)-2-oxindole

To a stirred solution of 2.8 g (0.12 mole) of sodium in 200 ml of ethanol was added 13.3 g (0.10 mole) of 2-oxindole, followed by 16.8 g of ethyl 3-furoate. The mixture was heated under reflux for 47 hours, cooled and then the solvent was removed by evaporation in vacuo. The residue was triturated under 200 ml of ether, and the solid was collected by filtration and discarded. The filtrate was evaporated in vacuo, and the residue triturated under isopropyl alcohol and recovered by filtration. The solid was suspended in 250 ml of water, which was then acidified with concentrated hydrochloric acid. This mixture was stirred to give a solid, which was recovered by filtration. This latter solid was recrystallized from acetic acid followed by acetonitrile to give 705 mg of the title compound, m.p. 185°–186° C.

Analysis: Calcd. for $C_{13}H_9O_3N$: C, 68.72; H, 3.99; N, 6.17%. Found: C, 68.72; H, 4.14; N, 6.14%.

PREPARATION 22

5-Amino-2-oxindole-1-carboxamide

To a solution of 5.0 g. of 5-nitro-2-oxindole-1-carboxamide in 110 ml. of N,N-dimethylformamide was added 0.5 g. of 10% palladium-on-carbon, and the resulting mixture was shaken under an atmosphere of hydrogen at an initial pressure of 5 kg/cm² until hydrogen uptake ceased. The catalyst was removed by filtration, and the filtrate was diluted with brine and extracted with ethyl acetate. The extracts were dried (MgSO₄) and evaporated in vacuo to give a dark-colored oil which solidified after trituration under water. This afforded 3.0 g. of the title compound as a yellow solid, mp 189°–191° C.

I claim:

1. A 2-oxindole-1-carboxamide compound of the formula:

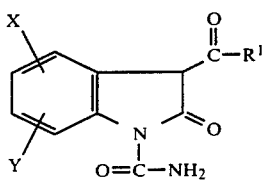

and the pharmaceutically-acceptable base salts thereof; wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7-ethylenedioxy group;

or X and Y when taken together and when attached to adjacent carbon atoms, form a divalent radical Z, wherein Z is selected from the group consisting of

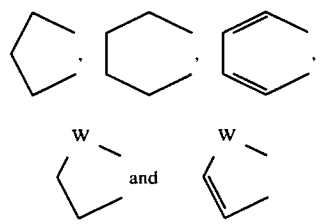

wherein W is oxygen or sulfur;

R¹ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)-alkyl having 1 to 3 carbons in said alkyl, naphthyl, bicyclo[2.2.1]heptan-2-yl, bicyclo[2.2.1]hept-5-en-2-yl and $—(CH_2)_n—Q—R°$;

wherein the substituent on said substituted phenyl, said (substituted phenyl)alkyl and said (substituted phenoxy)alkyl is selected from the group consisting of fluoro, bromo, chloro, alkyl having 1 to 4 carbons, alkoxy having 1 to 4 carbons and trifluoromethyl; n is zero, 1 or 2; Q is a divalent radical derived from a compound selected from the group consisting of furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b]thiophene; and R° is hydrogen or alkyl having 1 to 3 carbons.

2. A compound according to claim 1, wherein

X and Y are each selected from the group consisting of hydrogen, fluoro, chloro, bromo, alkyl having 1 to 4 carbons, alkoxy having 1 to 4 carbons, alkylthio having 1 to 4 carbons, nitro and trifluoromethyl;

or X and Y when taken together are a 4,5-, 5,6- or 6,7-methylenedioxy group;

and R¹ is selected from the group consisting of alkyl having 1 to 6 carbons, cycloalkyl having 3 to 7 carbons, phenyl, substituted phenyl, phenylalkyl having 1 to 3 carbons in said alkyl, phenoxyalkyl having 1 to 3 carbons in said alkyl, (substituted phenoxy)alkyl having 1 to 3 carbons in said alkyl, furyl, thienyl, pyrrolyl, alkylfuryl having 1 to 3 carbons in said alkyl, alkylthienyl having 1 to 3 carbons in said alkyl, furylalkyl having 1 to 3 carbons in said alkyl, thienylalkyl having 1 to 3 carbons in said alkyl and bicyclo[2.2.1]heptan-2-yl;

wherein the substituent on said substituted phenyl group and said substituted phenoxy group is selected from the group consisting of fluoro, chloro, bromo, alkyl having 1 to 4 carbons and alkoxy having 1 to 4 carbons.

3. A compound according to claim 2, wherein Y is hydrogen.

4. A compound according to claim 3, wherein X is selected from the group consisting of 5-chloro, 6-chloro, 5-fluoro, 6-fluoro, 5-trifluoromethyl and 6-trifluoromethyl.

5. A compound according to claim 4, wherein R¹ is selected from the group consisting of benzyl, 2-furyl, 2-thienyl, (2-furyl)methyl and (2-thienyl)-methyl 6. A compound according to claim 5, wherein X is 5-chloro or 6-chloro.

7. The compound according to claim 6, wherein X is 5-chloro and R¹ is 2-furyl.

8. The compound according to claim 6, wherein X is 5-chloro and R¹ is 2-thienyl.

9. The compound according to claim 6, wherein X is 6-chloro and R¹ is 2-thienyl.

10. A compound according to claim 5, wherein X is 5-fluoro or 6-fluoro.

11. The compound according to claim 10, wherein X is 5-fluoro and R¹ is (2-thienyl)methyl.

12. The compound according to claim 10, wherein X is 6-fluoro and R¹ is benzyl.

13. The compound according to claim 10, wherein X is 6-fluoro and R¹ is 2-thienyl.

14. A compound according to claim 5, wherein X is 5-trifluoromethyl or 6-trifluoromethyl.

15. The compound according to claim 14, wherein X is 5-trifluoromethyl and R¹ is (2-thienyl)methyl.

16. The compound according to claim 14, wherein X is 6-trifluoromethyl and R¹ is 2-furyl.

17. A compound according to claim 2, wherein X is selected from the group consisting of 5-chloro and 5-fluoro and Y is selected from the group consisting of 6-chloro and 6-fluoro.

18. A compound according to claim 17, wherein R¹ is selected from the group consisting of benzyl, 2-furyl, 2-thienyl, (2-furyl)methyl and (2-thienyl)-methyl.

19. The compound according to claim 18, wherein X is 5-fluoro, Y is 6-chloro and R¹ is benzyl.

20. A method of eliciting an analgesic response in a mammalian subject, which comprises administering to said mammalian subject an analgesic response eliciting amount of a 2-oxindole-1-carboxamide compound of the formula

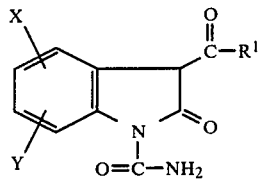

or a pharmaceutically-acceptable base salt thereof; wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7-ethylenedioxy group;

or X and Y when taken together and when attached to adjacent carbon atoms, form a divalent radical Z, wherein Z is selected from the group consisting of

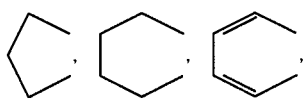

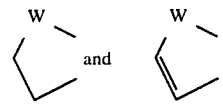

wherein W is oxygen or sulfur;

R¹ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)alkyl having 1 to 3 carbons in said alkyl, naphthyl, bicyclo[2.2.1]heptan-2-yl, bicyclo[2.2.1]hept-5-en-2-yl and —(CH$_2$)$_n$—Q—R°;

wherein the substituent on said substituted phenyl, said (substituted phenyl)alkyl and said (substituted phenoxy)alkyl is selected from the group consisting of fluoro, chloro, bromo, alkyl having 1 to 4 carbons, alkoxy having 1 to 4 carbons and trifluoromethyl; n is zero, 1 or 2; Q is a divalent radical derived from a compound selected from the group consisting of furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b]thiophene; and R° is hydrogen or alkyl having 1 to 3 carbons.

21. The method according to claim 20, wherein
X and Y are each selected from the group consisting of hydrogen, fluoro, chloro, bromo, alkyl having 1 to 4 carbons, alkoxy having 1 to 4 carbons, alkylthio having 1 to 4 carbons, nitro and trifluoromethyl;

or X and Y when taken together are a 4,5-, 5,6- or 6,7-methylenedioxy group;

R¹ is selected from the group consisting of alkyl having 1 to 6 carbons, cycloalkyl having 3 to 7 carbons, phenyl, substituted phenyl, phenylalkyl having 1 to 3 carbons in said alkyl, phenoxyalkyl having 1 to 3 carbons in said alkyl, (substituted phenoxy)alkyl having 1 to 3 carbons in said alkyl, furyl, thienyl, pyrrolyl, alkylfuryl having 1 to 3 carbons in said alkyl, alkylthienyl having 1 to 3 carbons in said alkyl, furylalkyl having 1 to 3 carbons in said alkyl, thienylalkyl having 1 to 3 carbons in said alkyl and bicyclo[2.2.1]heptan-2-yl;

wherein the substituent on said substituted phenyl group and said substituted phenoxy group is selected from the group consisting of fluoro, chloro, bromo, alkyl having 1 to 4 carbons and alkoxy having 1 to 4 carbons.

22. The method according to claim 21, wherein Y is hydrogen.

23. The method according to claim 22, wherein X is selected from the group consisting of 5-chloro, 6-chloro, 5-fluoro, 6-fluoro, 5-trifluoromethyl and 6-trifluoromethyl.

24. The method according to claim 23, wherein R¹ is selected from the group consisting of 2-furyl, 2-thienyl and (2-thienyl)methyl.

25. The method according to claim 24, wherein X is 5-chloro or 6-chloro.

26. The method according to claim 25, wherein X is 5-chloro and R¹ is 2-furyl.

27. The method according to claim 25, wherein X is 5-chloro and R¹ is 2-thienyl.

28. The method according to claim 25, wherein X is 6-chloro and R¹ is 2-thienyl.

29. The method according to claim 24, wherein X is 5-fluoro or 6-fluoro.

30. The method according to claim 29, wherein X is 5-fluoro and R¹ is (2-thienyl)methyl.

31. The method according to claim 29, wherein X is 6-fluoro and R¹ is benzyl.

32. The method according to claim 29, wherein X is 6-fluoro and R¹ is 2-thienyl.

33. The method according to claim 24, wherein X is 5-trifluoromethyl or 6-trifluoromethyl.

34. The method according to claim 33, wherein X is 5-trifluoromethyl and R¹ is (2-thienyl)methyl.

35. The method according to claim 33, wherein X is 6-trifluoromethyl and R¹ is 2-furyl.

36. The method according to claim 21, wherein X is selected from the group consisting of 5-chloro and 5-fluoro and Y is selected from the group consisting of 6-chloro and 6-fluoro.

37. The method according to claim 36, wherein R¹ is selected from the group consisting of benzyl, 2-furyl, 2-thienyl, (2-furyl)methyl and (2-thienyl)-methyl.

38. The method according to claim 37, wherein X is 5-fluoro, Y is 6-chloro and R¹ is benzyl.

39. A method of treating an inflammatory disease in a mammalian subject, which comprises administering to said mammalian subject an inflammatory disease treating amount of a 2-oxindole-1-carboxamide compound of the formula

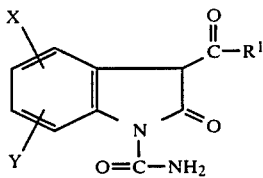

or a pharmaceutically-acceptable base salt thereof, wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7-ethylenedioxy group;

or X and Y when taken together and when attached to adjacent carbon atoms, form a divalent radical Z, wherein Z is selected from the group consisting of

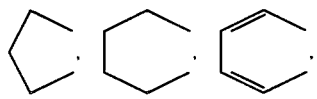

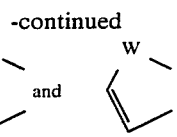

wherein W is oxygen or sulfur;

R¹ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)-alkyl having 1 to 3 carbons in said alkyl, naphthyl, bicyclo[2.2.1]heptan-2-yl, bicyclo[2.2.1]hept-5-en-2-yl and —(CH₂)ₙ—Q—R°;

wherein the substituent on said substituted phenyl, said (substituted phenyl)alkyl and said (substituted phenoxy)alkyl is selected from the group consisting of fluoro, chloro, bromo, alkyl having 1 to 4 carbons, alkoxy having 1 to 4 carbons and trifluoromethyl; n is zero, 1 or 2; Q is a divalent radical derived from a compound selected from the group consisting of furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b]-thiophene; and R° is hydrogen or alkyl having 1 to 3 carbons.

40. The method according to claim 39, wherein

X and Y are each selected from the group consisting of hydrogen, fluoro, chloro, bromo, alkyl having 1 to 4 carbons, alkoxy having 1 to 4 carbons, alkylthio having 1 to 4 carbons, nitro and trifluoromethyl;

or X and Y when taken together are a 4,5-, 5,6- or 6,7-methylenedioxy group;

R¹ is selected from the group consisting of alkyl having 1 to 6 carbons, cycloalkyl having 3 to 7 carbons, phenyl, substituted phenyl, phenylalkyl having 1 to 3 carbons in said alkyl, phenoxyalkyl having 1 to 3 carbons in said alkyl, (substituted phenoxy)alkyl having 1 to 3 carbons in said alkyl, furyl, thienyl, pyrrolyl, alkylfuryl having 1 to 3 carbons in said alkyl, alkylthienyl having 1 to 3 carbons in said alkyl, furylalkyl having 1 to 3 carbons in said alkyl, thienylalkyl having 1 to 3 carbons in said alkyl and bicyclo[2.2.1]heptan-2-yl;

wherein the substituent on said substituted phenyl group and said substituted phenoxy group is selected from the group consisting of fluoro, chloro, bromo, alkyl having 1 to 4 carbons and alkoxy having 1 to 4 carbons.

41. The method according to claim 40, wherein Y is hydrogen.

42. The method according to claim 41, wherein X is selected from the group consisting of 5-chloro, 6-chloro, 5-fluoro, 6-fluoro, 5-trifluoromethyl and 6-trifluoromethyl.

43. The method according to claim 42, wherein R¹ is selected from the group consisting of 2-furyl, 2-thienyl and (2-thienyl)methyl.

44. The method according to claim 43, wherein X is 5-chloro or 6-chloro.

45. The method according to claim 44, wherein X is 5-chloro and $R^1$ is 2-furyl.

46. The method according to claim 44, wherein X is 5-chloro and $R^1$ is 2-thienyl.

47. The method according to claim 44, wherein X is 6-chloro and $R^1$ is 2-thienyl.

48. The method according to claim 43, wherein X is 5-fluoro or 6-fluoro.

49. The method according to claim 48, wherein X is 5-fluoro and $R^1$ is (2-thienyl)methyl.

50. The method according to claim 48, wherein X is 6-fluoro and $R^1$ is benzyl.

51. The method according to claim 48, wherein x is 6-fluoro and $R^1$ is 2-thienyl.

52. The method according to claim 43, wherein X is 5-trifluoromethyl or 6-trifluoromethyl.

53. The method according to claim 52, wherein X is 5-trifluoromethyl and $R^1$ is (2-thienyl)methyl.

54. The method according to claim 52, wherein X is 6-trifluoromethyl and $R^1$ is 2-furyl.

55. The method to claim 40, wherein X is selected from the group consisting of 5-chloro and 5-fluoro and Y is selected from the group consisting of 6-chloro and 6-fluoro.

56. The method to claim 55, wherein $R^1$ is selected from the group consisting of benzyl, 2-furyl, 2-thienyl, (2-furyl)methyl and (2-thienyl)methyl.

57. The method according to claim 56, wherein X is 5-fluoro, Y is 6-chloro and $R^1$ is benzyl.

58. A pharmaceutical composition, useful as an analgesic and antiinflammatory agent in a mammalian subject, which comprises a pharmaceutically-acceptable carrier and an analgesic response eliciting or inflammatory disease treating amount of a 2-oxindole-1-carboxamide compound according to claim 1, and wherein the weight ratio of the pharmaceutically-acceptable carrier to the 2-oxindole-1-carboxamide compound is in the range from 1:4 to 4:1.

59. A compound of the formula

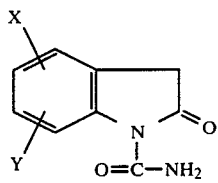

wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7-ethylenedioxy group;

or X and Y when taken together and when attached to adjacent carbon atoms, form a divalent radical Z, wherein Z is selected from the group consisting of

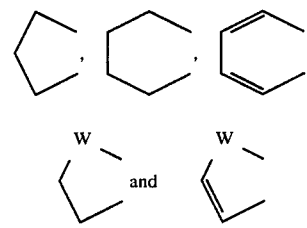

wherein W is oxygen or sulfur.

60. A compound according to claim 59, wherein X and Y are each selected from the group consisting of hydrogen, fluoro, chloro, bromo, alkyl having 1 to 4 carbons, alkoxy having 1 to 4 carbons, alkylthio having 1 to 4 carbons, nitro and trifluoromethyl; or X and Y when taken together are a 4,5-, 5,6- or 6,7-methylenedioxy group.

61. A compound according to claim 60, wherein Y is hydrogen and X is selected from the group consisting of 5-chloro, 6-chloro, 5-fluoro, 6-fluoro, 5-trifluoromethyl and 6-trifluoromethyl.

62. The compound according to claim 61, wherein X is 5-chloro.

63. The compound according to claim 61, wherein X is 5-trifluoromethyl.

64. A compound according to claim 59, wherein X is selected from the group consisting of 5-chloro and 5-fluoro and Y is selected from the group consisting of 6-chloro and 6-fluoro.

65. The compound according to claim 64, wherein X is 5-fluoro and Y is 6-chloro.

* * * * *